US005614532A

United States Patent [19]
Carling et al.

[11] Patent Number: 5,614,532
[45] Date of Patent: Mar. 25, 1997

[54] QUINOLONE DERIVATIVES

[75] Inventors: William R. Carling, Bishops Stortford; Paul D. Leeson, Cambridge; Michael Rowley, Harlow; Kevin W. Moore, Buntingford, all of Great Britain

[73] Assignee: Merck, Sharp & Dohme Ltd., Hoddesdon, England

[21] Appl. No.: 244,342

[22] PCT Filed: Nov. 25, 1992

[86] PCT No.: PCT/GB92/02183

§ 371 Date: May 25, 1994

§ 102(e) Date: May 25, 1994

[87] PCT Pub. No.: WO93/11115

PCT Pub. Date: Jun. 10, 1993

[30] Foreign Application Priority Data

Nov. 29, 1991 [GB] United Kingdom ............... 9125515

[51] Int. Cl.$^6$ ................ A61K 31/47; C07D 215/227
[52] U.S. Cl. ................................... 514/312; 546/157
[58] Field of Search ...................... 546/157; 514/312

[56] References Cited

U.S. PATENT DOCUMENTS

| | | | |
|---|---|---|---|
| 4,006,148 | 2/1977 | Wehrmeister | 546/155 |
| 5,348,962 | 9/1994 | Kulagowski et al. | 514/312 |

FOREIGN PATENT DOCUMENTS

| | | |
|---|---|---|
| 0386839A2 | 2/1990 | European Pat. Off. |
| 0481676A1 | 10/1991 | European Pat. Off. |
| 3526044A1 | 1/1987 | Germany . |
| 63295561 | 12/1988 | Japan . |

OTHER PUBLICATIONS

Stadlbauer, W., Montshefte fur Chemie, vol. 113, pp. 751–760, 1982.

Stadlbauer, W., Vestn. Slov. Kem. Drus., vol 33(3), pp. 271–281, 1986.

Chemical Abstracts 71:124273, 1969, abstract of JP 44016373, published Jul. 1969.

Chemical Abstracts 95:115244, 1981, abstract of an article by Stadlbauer, published vol 36B(6), pp. 739–744, 1981.

Chemical Abstracts 111:39201, 1988, abstract of JP 63295561, published Dec. 1988.

J. Chem. Soc. 1929, p. 2911, "Compounds of the Thioparaldehyde Type Derived from Chloral" by F. D. Chattaway and E. G. Kellett.

Monatsh. Chem., 1982, vol. 113, p. 751, "Isoquinolino[4,3-c]quinolines from Phenylmalonylheterocycles" by W. Stadlbauer and T. Kappe.

Vestn. Slov. Kem. Drus. vol. 33, No. 3, (1986), pp. 271–281, "Syntheses of Benzo-alpha and Benzo-gamma-carbolines via Azidoquinolines", by W. Stadlbauer and T. Kappa.

J. Heterocyclic Chem., vol. 26, pp. 281–284, (1989) "The Synthesis of Benzofuroquinolinws. IV." by S. Yamaguchi et al.

S. Yamaguchi, et al. Journal of Heterocyclic Chemistry, vol. 26, pp. 281–284, Mar.–Apr. 1989.

*Primary Examiner*—C. Warren Ivy
*Assistant Examiner*—D. Margaret M. Mach
*Attorney, Agent, or Firm*—Robert J. North; Melvin Winokur

[57] ABSTRACT

A class of 2-(1H)-quinolone derivatives, substituted at the 3-position by an optionally substituted aryl substituent, are selective non-competitive antagonists of NMDA receptors and/or are antagonists of AMPA receptors, and are therefore of utility in the treatment of conditions, such as neurodegenerative disorders, convulsions or schizophrenia, which require the administration of an NMDA and/or AMPA receptor antagonist.

7 Claims, No Drawings

QUINOLONE DERIVATIVES

This application is a 371 of PCT/GB92/02183, filed Nov. 25, 1992, and published as WO93/11115 Jun. 10, 1993.

This invention relates to a class of 2(1H)-quinolone derivatives which are substituted in the 3-position by an optionally substituted aryl substituent. These compounds are selective non-competitive antagonists of N-methyl-D-aspartate (NMDA) receptors. More particularly, the class of compounds provided by the present invention are ligands for the strychnine-insensitive glycine modulatory site of the NMDA receptor and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, *Neuroscience Lett.*, 1991, 121, 263; Murray et al., *Pain*, 1991, 44, 179; and Woolf and Thompson, *Pain*, 1991, 44, 293) and anxiolytic (see, for example, U.S. Pat. No. 5,145, 866; and Kehne et al., *Eur. J. Pharmacol.*, 1991, 193, 283) effects, and the compounds of the present invention may accordingly be useful in the management of pain and anxiety.

Compounds possessing functional antagonist properties for the NMDA receptor complex are stated in WO-A-91/19493 to be effective in the treatment of mood disorders, including major depression, bipolar disorder, dysthymia and seasonal affective disorder (cf. also Trullas and Skolnick, *Eur. J. Pharmacol.*, 1990, 185, 1). The compounds of the present invention may consequently be of benefit in the treatment and/or prevention of such disorders.

The association of NMDA receptor antagonists with regulation of the dopaminergic system has recently been reported (see, for example, Werling et al., *J. Pharmacol. Exp. Ther.*, 1990, 255, 40; Graham et al., *Life Sciences*, 1990, 47, PL-41; Hutson et al., *Br. J. Pharmacol.*, 1991, 103, 2037; and Turski et al., *Nature (London)*, 1991, 349, 414). This suggests that the compounds of the present invention may thus be of assistance in the prevention and/or treatment of disorders of the dopaminergic system such as schizophrenia and Parkinson's disease.

It has also been reported recently (see Lauritzen et al., *Journal of Cerebral Blood Flow and Metabolism*, 1991, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethylalk-3-ene carboxylic acids and esters described in EP-A-0420806, which are stated to be selective NMDA antagonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. By virtue of their activity as antagonists of NMDA receptors, therefore, the compounds of the present invention may be effective in controlling the manifestations of neuroviral diseases such as measles, rabies, tetanus (cf. Bagetta et al., *Br. J. Pharmacol.*, 1990, 101, 776) and AIDS (cf. Lipton et al., *Society for Neuroscience Abstracts*, 1990, 16, 128.11).

NMDA antagonists have, moreover, been shown to have an effect on the neuroendocrine system (see, for example, van den Pol et al., *Science*, 1990, 250, 1276; and Urbanski, *Endocrinology*, 1990, 127, 2223), and the compounds of this invention may therefore also be effective in the control of seasonal breeding in mammals.

In addition, certain compounds of the invention are antagonists of 2-amino-3-hydroxy-5-methyl-4-isoxazolepropionic acid (AMPA) receptors, also known as quisqualate receptors. An excitatory amino acid projection from the prefrontal cortex to the nucleus accumbens (a particular region of the forebrain possessing dopamine-sensitive neurones) is well known to exist (see, for example, *J. NeuroChem.*, 1985, 45, 477). It is also well known that dopaminergic transmission in the striatum is modulated by glutamate (see, for example, *Neurochem. Int.*, 1983, 5, 479), as also is the hyperactivity associated with presynaptic stimulation of the dopamine system by AMPA in the nucleus accumbens (cf. *Life Sci.*, 1981, 28, 1597). Compounds which are antagonists of AMPA receptors are therefore of value as neuroleptic agents.

A class of 3-phenyl-2(1H)-quinolone derivatives, substituted at the 4-position by an unsubstituted straight or branched alkoxy group containing 1 to 4 carbon atoms and at the 7-position by an unsubstituted straight or branched alkoxy group containing 2 to 10 carbon atoms or by a straight or branched alkoxy group containing 1 to 6 carbon atoms having at least one substituent selected from hydroxy, carboxy and carbamoyl, is described in JP-A-63-295561. These compounds are stated therein to exhibit a strong inhibitory action on bone resorption and a stimulatory effect on ossification, and thus to be useful as therapeutic agents for the prevention and treatment of osteoporosis.

A range of 3-(2-methoxyphenyl)-2(1H)-quinolones, possessing a halogen substituent in the 6- or 7-position and an optional carboxylic acid substituent at the 4-position, is described in *J. Heterocycl. Chem.*, 1989, 26, 281. The compound 4-carboxy-6-iodo-3-phenyl-2(1H)-quinolone is disclosed in *J. Chem. Soc.*, 1929, 2911.

A family of 3-phenyl-2(1H)-quinolone derivatives, substituted at the 4-position by an amino or benzylamino group and at the 7-position by a methyl or methoxy group, is described in *Monatsh. Chem.*, 1982, 113, 751; and *Vestn. Slov. Kem. Drus.*, 1986, 33, 271.

Except for JP-A-63-295561 as mentioned above, none of the aforementioned publications discloses any therapeutic utility for the various 3-phenyl-2(1H)-quinolone derivatives described therein. Moreover, in none of the prior art documents is there any suggestion that the compounds described therein would be of assistance in solving the problem of providing an effective agent for the treatment and/or prevention of conditions requiring the administration of an antagonist of NMDA and/or AMPA receptors.

The present invention accordingly provides the use of a compound of formula I or a pharmaceutically acceptable salt thereof or a prodrug thereof:

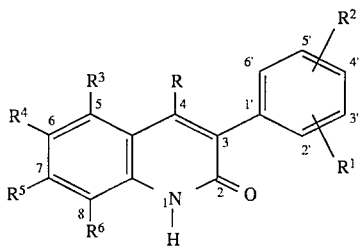

wherein

R represents a hydrogen atom, an amino group, a carboxy or $C_{2-6}$ alkoxycarbonyl group, or a group of formula -A-B-E, in which A represents a chemical bond, an oxygen or sulphur atom, or an —NH— group;

B represents a carbonyl (C=O) or sulphonyl ($SO_2$) group, or a straight or branched alkylene chain containing from 1 to 6 carbon atoms; and E represents $C_{2-6}$ alkyl, $C_{2-6}$ alkenyl, $C_{2-6}$ alkynyl, cyano, phenyl, tetrazolyl, methyloxadiazolyl, —$NR^aR^b$, —$COR^a$, —C(=N.$OR^a$)$R^b$, —$CO_2R^a$, —$CONR^aR^b$, —$CONR^a.OR^b$ or —$CH_2CO_2R^a$;

$R^1$ and $R^2$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; or $R^1$ and $R^2$ together represent the residue of a carbocyclic or heterocyclic ring;

one of $R^3$, $R^4$, $R^5$ and $R^6$ represents hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$, and the other three of $R^3$, $R^4$, $R^5$ and $R^6$ independently represent hydrogen, hydrocarbon, a heterocyclic group, halogen, cyano, trifluoromethyl, nitro, —$OR^a$, —$SR^a$, —$SOR^a$, —$SO_2R^a$, $SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group; for the manufacture of a medicament for the treatment and/or prevention of conditions, in particular neurodegenerative disorders, which require the administration of a selective non-competitive antagonist of NMDA receptors.

The present invention further provides the use of a compound of formula I as defined above or a pharmaceutically acceptable salt thereof or a prodrug thereof for the manufacture of a medicament for the treatment and/or prevention of conditions, such as schizophrenia, which require the administration of an antagonist of AMPA receptors.

The compounds of use in the present invention include those wherein E represents $C_{1-6}$ alkyl, alkenyl, phenyl, —$NR^aR^b$, —$CO_2R^a$ or —$CH_2CO_2R^a$; and the remaining substituents are as defined with reference to formula I above.

The compounds of formula I can exist as alternative tautomeric forms. It is to be understood that all tautomeric forms of the compounds of formula I, as well as all possible mixtures thereof, are included within the scope of the present invention.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{1-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

A particular aryl($C_{1-6}$)alkyl group is benzyl.

A particular aryl($C_{2-6}$)alkenyl group is phenylethenyl.

A particular aryl($C_{2-6}$)alkynyl group is phenylethynyl.

Suitable heterocycloalkyl groups include piperidyl, piperazinyl and morpholinyl groups.

A particular heterocycloalkyl($C_{1-6}$)alkyl group is morpholinylethyl.

Suitable heteroaryl groups include pyridyl, quinolyl, isoquinolyl, pyridazinyl, pyrimidinyl, pyrazinyl, pyrrolyl, indolyl, pyranyl, furyl, benzofuryl, thienyl, benzthienyl, imidazolyl, oxadiazolyl and thiadiazolyl groups. Particular heteroaryl groups are pyridyl, pyrrolyl, indolyl, furyl, benzofuryl, thienyl, benzthienyl and oxadiazolyl.

Particular heteroaryl($C_{1-6}$)alkyl groups include pyridylmethyl, pyrrolylmethyl, indolylmethyl, furylmethyl and thienylmethyl.

Where $R^1$ and $R^2$ together represent the residue of a carbocyclic or heterocyclic ring, the ring may be saturated or unsaturated. The ring may suitably be a 4- to 9-membered ring, but will preferably be a 5- or 6-membered ring. Where $R^1$ and $R^2$ together represent the residue of a heterocyclic ring, this ring may contain up to four heteroatoms selected from oxygen, nitrogen and sulphur. Suitable carbocyclic rings of which $R^1$ and $R^2$ together represent the residue include cyclohexane, cyclohexene, cyclohexadiene and benzene rings. Suitable heterocyclic rings of which $R^1$ and $R^2$ together represent the residue include dioxolane, dioxane, pyridine, furan, thiophene, pyrrole, thiazole and thiadiazole rings.

The hydrocarbon and heterocyclic groups, as well as the carbocyclic or heterocyclic ring completed by $R^1$ and $R^2$, may in turn be optionally substituted by one or more groups selected from $C_{1-6}$ alkyl, adamantyl, phenyl, halogen, $C_{1-6}$ haloalkyl, morpholinyl($C_{1-6}$)alkyl, trifluoromethyl, hydroxy, $C_{1-6}$ alkoxy, alkoxy($C_{1-6}$)alkyl, $C_{1-6}$ alkoxy($C_{1-6}$)alkoxy, aryloxy, keto, $C_{1-3}$ alkylenedioxy, nitro, cyano, carboxy, $C_{2-6}$ alkoxycarbonyl, $C_{2-6}$ alkoxycarbonyl$(C_{1-6})$alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, amino, mono- or di$(C_{1-6})$alkylamino, $C_{2-6}$ alkylcarbonylamino and $C_{2-6}$ alkoxycarbonylamino.

The term "halogen" as used herein includes fluorine, chlorine, bromine and iodine, especially chlorine.

When R in the compounds of formula I above represents a group of formula -A-B-E, and B represents a straight or branched alkylene chain containing from 1 to 6 carbon atoms, this alkylene chain may be, for example, methylene, ethylene, 1-methylethylene, propylene or 2-methylpropylene, preferably methylene, ethylene or propylene.

Examples of suitable substituents represented by the group R include hydrogen, carboxy$(C_{1-6})$alkoxy, alkoxycarbonyl$(C_{1-6})$alkoxy, $C_{3-10}$ alkenyloxy, $C_{2-6}$ alkynyloxy, cyano$(C_{1-6})$alkoxy, amino$(C_{1-6})$alkoxy, di$(C_{1-6})$alkylamino$(C_{1-6})$alkoxy, $C_{1-6}$alkanoyl$(C_{1-6})$alkoxy, oximino$(C_{1-6})$alkoxy, $C_{1-6}$ alkyloximino$(C_{1-6})$alkoxy, aminocarbonyl$(C_{1-6})$alkoxy, di$(C_{1-6})$aminocarbonyl$(C_{1-6})$alkoxy, $C_{1-6}$ alkoxyaminocarbonyl$(C_{1-6})$alkoxy, amino, phenyl$(C_{1-6})$alkylamino, amino$(C_{1-6})$alkylamino, di$(C_{1-6})$alkylamino$(C_{1-6})$alkylamino, carboxy$(C_{1-6})$alkylamino, $C_{2-6}$ alkanoylamino, carboxy-carbonylamino, $C_{2-6}$ alkoxycarbonyl-carbonylamino, carboxymethylcarbonylamino, $C_{2-6}$ alkoxycarbonylmethyl-carbonylamino, $C_{1-6}$ alkylsulphonylamino, phenylsulphonylamino, carboxy, $C_{2-6}$ alkoxycarbonyl, carboxy$(C_{1-6})$alkyl, $C_{2-6}$ alkoxycarbonyl$(C_{1-6})$alkyl, cyano$(C_{1-6})$alkyl, tetrazolyl$(C_{1-6})$alkyl, methyloxadiazolyl$(C_{1-6})$alkyl and aminocarbonyl$(C_{1-6})$alkyl.

Particular examples of the substituent R include hydrogen, carboxy-methoxy, methoxycarbonylmethoxy, allyloxy, propynyloxy, cyano-methoxy, dimethylamino-ethoxy, methylcarbonyl-methoxy, oximinopropyloxy, methyloximinopropyloxy, aminocarbonylmethoxy, dimethylaminocarbonyl-methoxy, methoxyaminocarbonyl-methoxy, amino, benzylamino, dimethylamino-ethylamino, dimethylaminopropylamino, acetylamino, carboxymethyl-carbonylamino, carboxycarbonylamino, methoxycarbonyl-carbonylamino, methylsulphonylamino, phenylsulphonylamino, carboxy, methoxycarbonyl, carboxymethyl, methoxycarbonyl-methyl, carboxyethyl, methoxycarbonyl-ethyl, cyanoethyl, tetrazolyl-ethyl, methyloxadiazolyl-ethyl and aminocarbonyl-ethyl.

Suitable values for the substituents $R^1$ and $R^2$ include $C_{1-6}$ alkyl, aryl, aryl$(C_{1-6})$alkyl, aryl$(C_{2-6})$alkenyl, aryl$(C_{2-6})$alkynyl, heteroaryl$(C_{1-6})$alkyl, $C_{1-6}$ alkoxy, $C_{2-6}$ alkenyloxy, aryloxy, aryl$(C_{1-6})$alkoxy, heteroaryloxy, arylthio, arylsulphonyl, arylamino, aryl$(C_{1-6})$alkylamino, di$(C_{1-6})$alkylamino, arylcarbonylamino, arylcarbonyl or heteroarylcarbonyl, any of which groups may be optionally substituted; and hydrogen, halogen, trifluoromethyl, nitro, hydroxy or carboxy. Examples of optional substituents on the groups $R^1$ and/or $R^2$ include $C_{1-6}$ alkyl, morpholinyl$(C_{1-6})$alkyl, hydroxy, $C_{1-6}$ alkoxy, $C_{1-6}$ alkoxy$(C_{1-6})$alkyl, $C_{1-6}$ alkoxy$(C_{1-6})$alkoxy, $C_{1-6}$ alkylthio and di$(C_{1-6})$alkylamino.

Particular values for the substituents $R^1$ and $R^2$ include hydrogen, methyl, phenyl, benzyl, methoxymethylbenzyl, morpholinylethyl-benzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, hydroxy, methoxy, ethoxy, allyloxy, methyl-allyloxy, phenoxy, methyl-phenoxy, methoxy-phenoxy, dimethylamino-phenoxy, benzyloxy, furyloxy, thienyloxy, pyridyloxy, phenylthio, phenylsulphonyl, amino, phenylamino, benzylamino, dimethylamino, phenylcarbonylamino, phenylcarbonyl, furylcarbonyl, thienylcarbonyl and carboxy, especially hydroxy, methoxy, phenoxy, amino and carboxy.

Suitably, one of $R^1$ and $R^2$ represents hydrogen. Preferably, at least one of $R^1$ and $R^2$ is other than hydrogen.

Where $R^1$ and $R^2$ together represent the residue of a carbocyclic or heterocyclic ring, this may be, in particular, a dioxolane or optionally substituted benzene ring.

The benzo moiety of the 2(1H)-quinolone ring system shown in formula I above contains at least one non-hydrogen substituent. Particular substituents include halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio and $C_{2-7}$ alkoxycarbonyl. Suitably $R^6$ is hydrogen and $R^3$, $R^4$ and $R^5$ independently represent hydrogen, halogen, cyano, trifluoromethyl, nitro, $C_{1-6}$ alkyl or $C_{2-6}$ alkenyl, provided that at least one of $R^2$, $R^4$ and $R^5$ is other than hydrogen. Preferably, $R^4$ and $R^6$ each represents hydrogen, one of $R^3$ and $R^5$ represents cyano, trifluoromethyl, nitro, methyl, ethyl, vinyl or halogen, especially chlorine or iodine, and the other of $R^3$ and $R^5$ represents hydrogen, cyano, trifluoromethyl, nitro, methyl, ethyl, vinyl or halogen, especially chlorine or iodine. In a particular embodiment, $R^5$ represents cyano, trifluoromethyl, nitro or halogen, especially chlorine; and $R^3$ is hydrogen or ethyl.

In a further aspect, the invention provides a pharmaceutical composition comprising a compound of formula IA or a pharmaceutically acceptable salt thereof or a prodrug thereof:

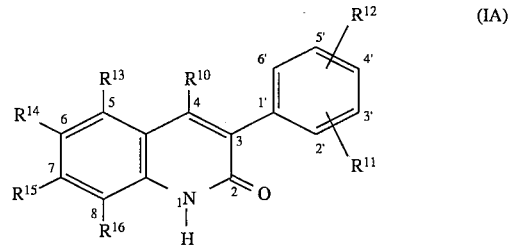

(IA)

wherein $R^{10}$ represents a hydrogen atom, an amino group, a carboxy or $C_{2-6}$ alkoxycarbonyl group, or a group of formula -A-B-E, in which A represents a chemical bond, an oxygen or sulphur atom, or an —NH— group;

B represents a carbonyl (C=O) or sulphonyl ($SO_2$) group, or a straight or branched alkylene chain containing from 1 to 6 carbon atoms; and E represents $C_{1-6}$ alkyl, $C_{2-6}$ alkenyl, $C_{2-6}$ alkynyl, cyano, phenyl, tetrazolyl, methyloxadiazolyl, —$NR^aR^b$, —$COR^a$, —C(=N.$OR^a$)$R^b$, —$CO_2R^a$, —$CONR^aR^b$, —$CONR^a.OR^b$ or —$CH_2CO_2R^a$;

$R^{11}$ and $R^{12}$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^B$, —$NR^aR^b$, —$NR^aCOR^b$, —$NR^aCO_2R^b$, —$COR^a$, —$CO_2R^a$ or —$CONR^aR^b$; or $R^{11}$ and $R^{12}$ together represent the residue of a carbocyclic or heterocyclic ring;

one of $R^{13}$, $R^{14}$, $R^{15}$ and $R^{16}$ represents hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, $COR^a$, —$CO_2R^a$ or —$CONR^aR^B$, and the other three of $R^{13}$, $R^{14}$, $R^{15}$ and $R^{16}$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^B$, —$NR^aR^B$, —$NR^aCOR^B$, —$NR^aCO_2R^b$, —$COR^a$, —$CO_2R^a$ or —$CONR^aR^b$; and $R^a$ and $R^b$ independently represent hydrogen, hydrocarbon or a heterocyclic group;

provided that, when $R^{10}$ represents a straight or branched alkoxy group containing 2 to 4 carbon atoms and $R^{11}$, $R^{12}$, $R^{13}$, $R^{14}$ and $R^{16}$ each represents hydrogen, then $R^{15}$ does not represent an unsubstituted straight or branched alkoxy group containing 2 to 10 carbon atoms or a straight or branched alkoxy group containing 1 to 6 carbon atoms having at least one substituent selected from hydroxy, carboxy and carbamoyl;

provided also that when $R^{10}$, $R^{11}$, $R^{14}$ and $R^{16}$ each represents hydrogen and $R^{12}$ represents hydrogen or methoxy in the 4'-position, then:

(i) $R^{15}$ does not represent hydrogen when $R^{13}$ is chloro; and (ii) $R^{13}$ does not represent hydrogen when $R^{15}$ is chloro or dimethylamino;

in association with one or more pharmaceutically acceptable carriers and/or excipients.

The invention also provides a compound of formula IA as defined above or a pharmaceutically acceptable salt thereof or a prodrug thereof for use in therapy.

Subject to the above proviso, the substituents $R^{10}$ and $R^{11}$ to $R^{16}$ in the compounds of formula IA correspond to the substituents R and $R^1$ to $R^6$ respectively as defined with reference to the compounds of formula I.

Particular pharmaceutical compositions according to the invention contain, as the active ingredient, at least one of the following compounds: 7-chloro-3-(2-methoxyphenyl)-2(1H)-quinolone; and pharmaceutically acceptable salts thereof and prodrugs thereof.

Certain compounds falling within the definition of formula I above are novel. Accordingly, in a still further aspect the present invention provides a compound of formula IB or a salt or prodrug thereof:

(IB)

wherein $R^{20}$ represents a hydrogen atom, an amino group, a carboxy or $C_{2-6}$ alkoxycarbonyl group, or a group of formula -A-B-E, in which A represents a chemical bond, an oxygen or sulphur atom, or an —NH— group;

B represents a carbonyl (C=O) or sulphonyl ($SO_2$) group, or a straight or branched alkylene chain containing from 1 to 6 carbon atoms; and E represents $C_{16}$ alkyl, $C_{2-6}$ alkenyl, $C_{2-6}$ alkynyl, cyano, phenyl, tetrazolyl, methyloxadiazolyl, —$NR^aR^b$, —$COR^a$, —$C(=N.OR^a)R^b$, —$CO_2R^a$, —$CONR^aR^b$, —$CONR^a.OR^b$ or —$CH_2CO_2R^a$;

$R^{21}$ and $R^{22}$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; or $R^{21}$ and $R^{22}$ together represent the residue of a carbocyclic or heterocyclic ring;

one of $R^{23}$, $R^{24}$, $R^{25}$ and $R^{26}$ represents hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$, and the other three of $R^{23}$, $R^{24}$, $R^{25}$ and $R^{26}$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group;

provided that, when $R^{21}$ and $R^{22}$ each represents hydrogen, then:

(i) $R^{25}$ does not represent an unsubstituted straight or branched alkoxy group containing 2 to 10 carbon atoms or a straight or branched alkoxy group containing 1 to 6 carbon atoms having at least one substituent selected from hydroxy, carboxy and carbamoyl when $R^{20}$ represents a straight or branched alkoxy group containing 2 to 4 carbon atoms and $R^{23}$, $R^{24}$ and $R^{26}$ each represents hydrogen; and (ii) $R^{20}$ does not represent carboxy when $R^{24}$ is iodo and $R^{23}$, $R^{25}$ and $R^{26}$ each represents hydrogen; and (iii) $R^{20}$ does not represent amino or benzylamino when $R^{25}$ represents methyl or methoxy and $R^{23}$, $R^{24}$ and $R^{26}$ each represent hydrogen;

provided also that when $R^{21}$ is 2'-methoxy and $R^{22}$, $R^{23}$ and $R^{26}$ each represents hydrogen, then:

(i) $R^{20}$ does not represent hydrogen or carboxy when one of $R^{24}$ and $R^{25}$ represents fluoro or chloro and the other is hydrogen; and (ii) $R^{20}$ does not represent carboxy when one of $R^{24}$ and $R^{25}$ represents bromo or iodo and other is hydrogen;

further provided that, when $R^{20}$ and $R^{21}$ each represents hydrogen, one of $R^{23}$, $R^{24}$, $R^{25}$ and $R^{26}$ represents chloro, nitro or dimethylamino and the other three of $R^{23}$, $R^{24}$, $R^{25}$ and $R^{26}$ each represents hydrogen, then $R^{22}$ does not represent hydrogen or methoxy in the 4'-position.

Subject to the above provisos, the substituents $R^{20}$ and $R^{21}$ to $R^{26}$ in the compounds of formula IB correspond to the substituents R and $R^1$ to $R^6$ respectively as defined with reference to the compounds of formula I.

For use in medicine, the salts of the compounds of formula IB will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formulae I, IA and IB above include alkali metal salts, e.g. lithium, sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid or phosphoric acid.

The present invention includes within its scope prodrugs of the compounds of formulae I, IA and IB above. In general, such prodrugs will be functional derivatives of the compounds of formulae I, IA and IB which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA and salts and prodrugs thereof:

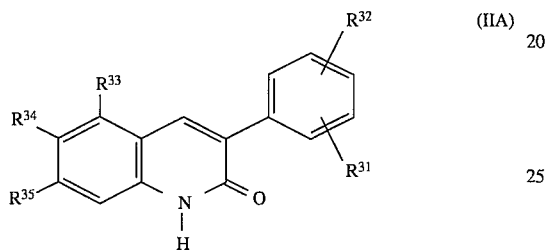

wherein $R^{31}$ represents $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$)alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or $C_{2-7}$ alkoxycarbonyl, any of which groups may be optionally substituted; or hydrogen, halogen, cyano, trifluoromethyl, nitro, hydroxy, amino or carboxy; and $R^{32}$ represents $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl,($C_{2-6}$)alkoxy,($C_{2-6}$) alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or ($C_{2-7}$)alkoxycarbonyl, any of which groups may be optionally substituted; or halogen, cyano, trifluoromethyl, nitro, hydroxy, amino or carboxy; or $R^{31}$ and $R^{32}$ together represent the residue of a carbocyclic or heterocyclic ring;

$R^{33}$ represents hydrogen, halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or($C_{2-7}$) alkoxycarbonyl;

$R^{34}$ represents hydrogen or halogen; and $R^{35}$ represents halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl.

Examples of optional substituents on the groups $R^{31}$ and/or $R^{32}$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$) alkoxy, $C_{1-6}$ alkylthio and di($C_{1-6}$)alkylamino.

Particular values of $R^{31}$ with respect to formula IIA include hydrogen, hydroxy, methoxy, phenoxy, amino and carboxy, preferably hydrogen or methoxy. Particular values of $R^{32}$ with respect to formula IIA include hydroxy, phenoxy, amino and carboxy.

In an especial embodiment, $R^{31}$ is hydrogen and $R^{32}$ is hydroxy, amino or carboxy.

Suitably, $R^{33}$ represents hydrogen, nitro, methyl, ethyl, vinyl or halogen, especially chlorine or iodine. Preferably, $R^{33}$ is hydrogen, ethyl or iodine.

Suitably, $R^{34}$ represents hydrogen or chlorine, preferably hydrogen.

Suitably, $R^{35}$ represents cyano, trifluoromethyl, nitro, methyl or halogen, preferably chlorine.

Another sub-class of compounds according to the invention is represented by the compounds of formula IIB and salts and prodrugs thereof:

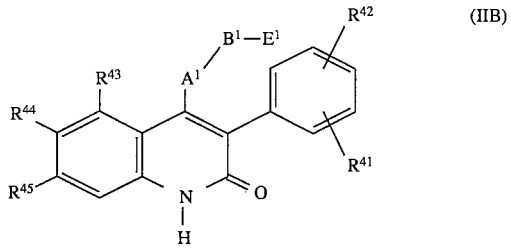

wherein $A^1$ represents a chemical bond, an oxygen atom or an —NH— group;

$B^1$ represents a carbonyl (C=O) or sulphonyl (SO$_2$) group, or a group of formula —(CH$_2$)$_n$— in which n is 1, 2, 3 or 4; and $E^1$ represents $C_{1-6}$ alkyl, $C_{2-6}$ alkenyl, $C_{2-6}$ alkynyl, cyano, phenyl, tetrazolyl, methyloxadiazolyl, amino, $C_{1-6}$ alkylamino, di($C_{1-6}$)alkylamino, $C_{1-6}$ alkanoyl, oximino($C_{1-6}$)alkyl, $C_{1-6}$ alkyloximino($C_{1-6}$)alkyl, carboxy, $C_{2-6}$ alkoxycarbonyl, aminocarbonyl, di($C_{1-6}$)alkylaminocarbonyl, $C_{1-6}$ alkoxyaminocarbonyl, carboxymethyl or $C_{2-6}$ alkoxycarbonyl-methyl;

$R^{41}$ and $R^{42}$ independently represent $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or $C_{2-7}$ alkoxycarbonyl, any of which groups may be optionally substituted; or hydrogen, halogen, cyano, trifluoromethyl, nitro, hydroxy, amino or carboxy; or $R^{41}$ and $R^{42}$ together represent the residue of carbocyclic or heterocyclic ring;

$R^{43}$ and $R^{44}$ independently represent hydrogen, halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl; and $R^{45}$ represents halogen, cyano, trifluoromethyl, nitro, hydroxy, amino, carboxy, $C_{2-6}$ alkenyl, $C_{1-6}$ alkylthio or $C_{2-7}$ alkoxycarbonyl.

Examples of optional substituents on the groups $R^{41}$ and/or $R^{42}$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$)alkylamino.

Particular examples of the substituent -A$^1$-B$^1$-E$^1$ with reference to formula IIB include carboxymethyl, methoxycarbonyl-methyl, carboxyethyl, methoxycarbonylethyl, cyanoethyl, tetrazolyl-ethyl, methyloxadiazolylethyl, aminocarbonyl-ethyl, carboxymethoxy, methoxycarbonyl-methoxy, allyloxy, propynyloxy, cyanomethoxy, dimethylaminoethoxy, methylcarbonyl-methoxy, oximino-propyloxy, methyloximino-propyloxy, aminocarbonyl-methoxy, dimethylaminocarbonyl-methoxy, methoxyaminocarbonylmethoxy, benzylamino, dimethylaminoethylamino, dimethylamino-propylamino, acetylamino, carboxymethyl-carbonylamino, carboxy-carbonylamino, methoxycarbonylcarbonylamino, methylsulphonylamino and phenylsulphonylamino.

Particular values of $R^{41}$ and/or $R^{42}$ with respect to formula IIB include hydrogen, methyl, phenyl, benzyl, methoxymethyl-benzyl, morpholinylethyl-benzyl, hydroxybenzyl, methoxybenzyl, methoxymethoxy-benzyl, methylthiobenzyl, phenylethenyl, phenylethynyl, thienylmethyl, pyrrolylmethyl, indolylmethyl, fluoro, chloro, bromo, iodo, trifluoromethyl, nitro, hydroxy, methoxy, ethoxy, allyloxy, methyl-allyloxy, phenoxy, methyl-phenoxy, methoxy-phenoxy, dimethylamino-phenoxy, benzyloxy, furyloxy, thienyloxy, pyridyloxy, phenylthio, phenylsulphonyl, amino, phenylamino, benzylamino, dimethylamino, phenylcarbonylamino, phenylcarbonyl, furylcarbonyl, thienylcarbonyl and carboxy. Moreover, $R^{41}$ and $R^{42}$ may suitably together represent the residue of a dioxolane or optionally substituted benzene ring.

Preferably, one of $R^{41}$ and $R^{42}$ represents hydrogen and the other represents hydrogen, hydroxy, methoxy, phenoxy, amino or carboxy.

Suitably, $R^{43}$ and $R^{44}$ independently represent hydrogen, nitro, methyl, ethyl, vinyl or halogen, especially chlorine or iodine. Preferably, $R^{43}$ is hydrogen, ethyl or iodine. Preferably, $R^{44}$ is hydrogen.

Suitably, $R^{45}$ represents cyano, trifluoromethyl, nitro or halogen, preferably chlorine.

Specific compounds within the scope of the present invention include:

7-chloro-3-(2-hydroxyphenyl)-2(1H)-quinolone;
7-chloro-3-(4-hydroxyphenyl)-2(1H)-quinolone;
3-(2-aminophenyl)-7-chloro-2(1H)-quinolone;
3-(3-carboxyphenyl)-7-chloro-2(1H)-quinolone;
4-carboxy-7-chloro-3-phenyl-2(1H)-quinolone;
4-carboxymethyl-7-chloro-3-phenyl-2(1H)-quinolone;
7-chloro-4-methoxycarbonylmethyl-3-phenyl-2(1H)-quinolone;
4-carboxymethoxy-7-chloro-3-phenyl-2(1H)-quinolone;
7-chloro-4-methoxycarbonylmethoxy-3-phenyl-2(1H)-quinolone;
4-allyloxy-7-chloro-3-phenyl-2(1H)-quinolone;
4-amino-7-chloro-3-phenyl-2(1H)-quinolone;
4-amino-7-chloro-3-(2-methoxyphenyl)-2(1H)-quinolone;
4-amino-7-chloro-3-(3-phenoxyphenyl)-2(1H)-quinolone;
4-benzylamino-7-chloro-3-phenyl-2(1H)-quinolone;
7-chloro-4-(2-dimethylaminoethyl)amino-3-phenyl-2(1H)-quinolone;
7-chloro-4-(3-dimethylaminopropyl)amino-3-phenyl-2(1H)-quinolone;
4-acetylamino-7-chloro-3-phenyl-2(1H)-quinolone;
4-carboxymethylcarbonylamino-7-chloro-3-phenyl-2(1H)-quinolone;
4-carboxycarbonylamino-7-chloro-3-phenyl-2(1H)-quinolone;
7-chloro-4-methoxycarbonylcarbonylamino-3-phenyl-2(1H)-quinolone;
7-chloro-4-methylsulphonylamino-3-phenyl-2(1H)-quinolone;
7-chloro-3-phenyl-4-phenylsulphonylamino-2(1H)-quinolone;
7-chloro-4-methylcarbonylmethoxy-3-phenyl-2(1H)-quinolone;
7-chloro-4-(2-oximinopropyl)oxy-3-phenyl-2(1H)-quinolone;
7-chloro-3-phenyl-4-(2-propynyl)oxy-2(1H)-quinolone;
7-chloro-4-(2-methyloximinopropyl)oxy-3-phenyl-2(1H)-quinolone;
7-chloro-4-methoxycarbonylmethoxy-3-(3-phenoxyphenyl)-2(1H)-quinolone;
4-carboxymethoxy-7-chloro-3-(3-phenoxyphenyl)-2(1H)-quinolone;
7-chloro-4-cyanomethoxy-3-phenyl-2(1H)-quinolone;
7-chloro-4-cyanomethoxy-3-(3-phenoxyphenyl)-2(1H)-quinolone;
7-chloro-4-(N,N-dimethylaminocarbonyl)methoxy-3-phenyl-2(1H)-quinolone;
7-chloro-4-[2-(N,N-dimethylamino)ethoxy]-3-Phenyl-2(1H)-quinolone;
4-aminocarbonylmethoxy-7-chloro-3-phenyl-2(1H)-quinolone;
7-chloro-4-methoxyaminocarbonylmethoxy-3-phenyl-2(1H)-quinolone;
7-chloro-4-(2-methoxycarbonylethyl)-3-phenyl-2(1H)-quinolone;
4-(2-carboxyethyl)-7-chloro-3-phenyl-2(1H)-quinolone;
4-(2-aminocarbonylethyl)-7-chloro-3-phenyl-2(1H)-quinolone;
7-chloro-4-(2-cyanoethyl)-3-phenyl-2(1H)-quinolone;
7-chloro-3-phenyl-4-[2-(1H-tetrazol-5-yl)ethyl]-2(1H)-quinolone;
7-chloro-4-[2-(3-methyl-1,2,4-oxadiazol-5-yl)ethyl]-3-phenyl-2(1H)-quinolone;
and salts and prodrugs thereof.

The pharmaceutical compositions of this invention are preferably in unit dosage forms such as tablets, pills, capsules, powders, granules, sterile solutions or suspensions, or suppositories, for oral, intravenous, parenteral or rectal administration. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can 10 comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

The compounds of formula I above wherein R represents hydrogen, amino or a group of formula -A-B-E in which A represents a chemical bond and B is a straight or branched alkylene chain containing from 1 to 6 carbon atoms, including the novel compounds according to the invention, may be prepared by a process which comprises cyclising a compound of formula III:

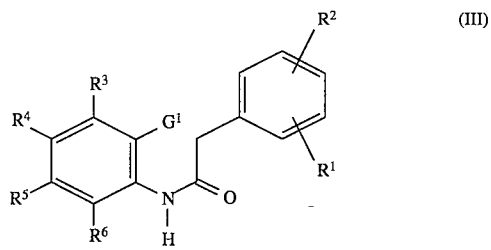

wherein $R^1$, $R^2$, $R^3$, $R^4$, $R^5$ and $R^6$ are as defined above; and $G^1$ represents an aldehyde (—CHO) or cyano (—CN) group, or a group of formula —CO—$B^a$—E in which $B^a$ represents a straight or branched alkylene chain containing from 1 to 6 carbon atoms and E is as defined above.

The reaction is conveniently carried out in the presence of a base, followed by a mild acidic work-up. Suitable bases of use in the reaction include sodium methoxide, sodium hydride and potassium hexamethyldisilazide.

When $G^1$ in the compounds of formula III above represents an aldehyde group, the product of the reaction is a compound of formula I wherein R is hydrogen. When $G^1$ represents a cyano group, the product of the reaction is a compound of formula I wherein R is an amino group. When $G^1$ represents a group of formula —CO—$B^a$—E, the product of the reaction is a compound of formula I wherein R is a group of formula -A-B-E in which A represents a chemical bond and B is a straight or branched alkylene group containing from 1 to 6 carbon atoms.

The compounds of formula I wherein R represents a group of formula -A-B-E in which A represents a chemical bond, B is a methylene group and E represents —$CO_2R^a$ may be prepared by intramolecular Michael cyclisation of a compound of formula IIIA:

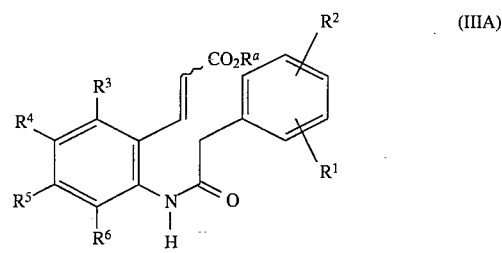

wherein $R^1$, $R^2$, $R^3$, $R^4$, $R^5$, $R^6$ and $R^a$ are as defined above; in the presence of a strong base, e.g. sodium methoxide; followed by quenching with a selenyl halide reagent, e.g. phenylselenyl chloride; and subsequent elimination of selenium to afford the double bond in the 3,4-position.

The intermediates of formulae III and IIIA above may conveniently be prepared by reacting a compound of formula IV with a compound of formula V:

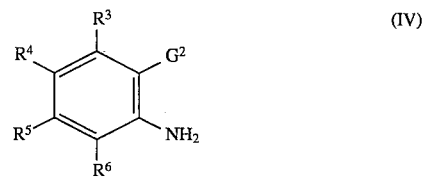

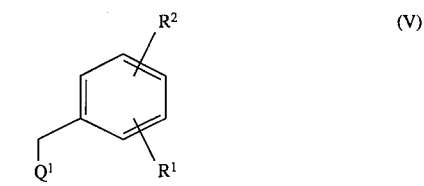

wherein $R^1$, $R^2$, $R^3$, $R^4$, $R^5$ and $R^6$ are as defined above; $G^2$ corresponds to the group $G^1$ as defined above or represents a group of formula —CH=CH.$CO_2R^a$ in which $R^a$ is as defined above; and $Q^1$ represents a reactive carboxylate moiety.

The reaction is conveniently effected by mixing the reagents in an inert solvent, such as dichloromethane or 1,2-dichloroethane, and heating the reaction mixture at an elevated temperature, for example the reflux temperature of the solvent employed.

Suitable values for the reactive carboxylate moiety $Q^1$ include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Preferably, the group $Q^1$ is an acid halide group, in particular an acid chloride group. A compound of formula V wherein $Q^1$ represents an acid chloride group may conveniently be prepared from the corresponding compound of formula V wherein $Q^1$ represents a carboxy group —$CO_2H$ (i.e. a compound of formula VA as defined below) by treatment with oxalyl chloride or thionyl chloride under standard conditions well known from the art.

The compounds of formula I wherein R represents a carboxy group, including the novel compounds according to the invention, may be prepared by a process which comprises reacting a compound of formula VI with a compound of formula VA:

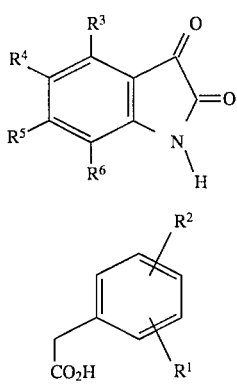

wherein $R^1$, $R^2$, $R^3$, $R^4$, $R^5$ and $R^6$ are as defined above.

The reaction is conveniently carried out in the presence of sodium acetate at an elevated temperature, e.g. 200° to 230° C., as described, for example, in *J. Heterocycl. Chem.*, 1989, 26, 281.

The compounds of formula I wherein R represents a group of formula -A-B-E in which A represents an oxygen or sulphur atom or an —NH— group, including the novel compounds according to the invention, may be prepared by reacting a compound of formula L-B-E with a compound of formula VII:

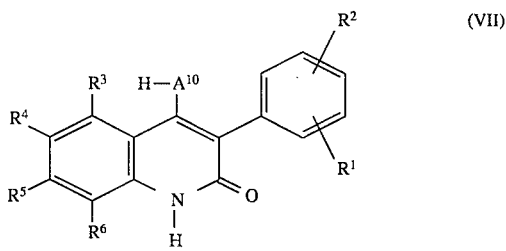

wherein $R^1$, $R^2$, $R^3$, $R^4$, $R^5$, $R^6$, B and E are as defined above; $A^{10}$ represents an oxygen or sulphur atom or an —NH— group; and L represents a leaving group such as a halogen atom, e.g. chloro or bromo.

The reaction is conveniently carried out in the presence of a base. When $A^{10}$ represents oxygen or sulphur, a mild base such as sodium bicarbonate is advantageously employed, and the reaction is suitably effected in a solvent such as N,N-dimethylformamide. When $A^{10}$ represents an —NH— group, a preferred base, depending upon the nature of the reagent L-B-E, is sodium hydride or potassium hexamethyldisilazide, and the reaction is advantageously effected in a compatible solvent, such as tetrahydrofuran.

In an alternative process, the compounds of formula I wherein R represents a group of formula -A-B-E in which A represents an —NH— group, including the novel compounds according to the invention, may be prepared by reacting a compound of formula $H_2N$-B-E, wherein B and E are as defined above, with a compound of formula VII above wherein $A^{10}$ represents an oxygen atom.

The reaction is conveniently effected by heating the reagents together at the reflux temperature of the mixture, as described, for example, in *Vestn. Slov. Kem. Drus.*, 1986, 33, 271; or, if necessary, by maintaining the reaction mixture at an elevated temperature for several days in a sealed tube.

A given intermediate of formula VII above wherein $A^{10}$ represents sulphur may be prepared from the corresponding compound of formula VII wherein $A^{10}$ represents oxygen by treating the latter compound firstly with N,N-dimethylthiocarbamyl chloride and then with a mineral acid such as hydrochloric acid, followed by hydrolysis with base, e.g. sodium hydroxide, by analogy with the procedure described in WO-A-91/01973.

The intermediates of formula VII above wherein $A^{10}$ represents oxygen may be prepared by the procedures described in EP-A-0481676, or by methods analogous thereto. Additional sources of reference for preparing compounds corresponding to those of formula VII above wherein $A^{10}$ represents oxygen include, for example, *J. Heterocycl. Chem.*, 1975, 12, 351; and ibid., 1988, 25, 857.

The aromatic intermediates of formulae IV, V, VA and VI above, where they are not commercially available, may be prepared by the methods described in the accompanying Examples, or by methods analogous thereto which will be readily apparent to those skilled in the art.

As will be appreciated, the compounds of formula VII above wherein $A^{10}$ represents an —NH— group, which can be used as intermediates in the preparation of compounds in accordance with the present invention, are themselves compounds according to the invention. It is to be understood that any compound of formula I, IA or IB initially obtained from any of the above processes may, where appropriate, subsequently be elaborated into a further desired compound of formula I, IA or IB respectively using techniques known from the art. For example, a compound of formula I initially obtained wherein R is carboxy may be converted into a corresponding compound of formula I wherein R represents a $C_{1-6}$ alkoxycarbonyl group by standard esterification procedures common in the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (–)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently and selectively block responses to NMDA and/or AMPA in a brain slice from rat cortex, and inhibit the binding of agonists and antagonists to the strychnine-insensitive site present on the NMDA receptor and/or AMPA binding to rat forebrain membranes.

Cortical Slice Studies

The effects of compounds of the invention on responses to NMDA and AMPA were assessed using the rat cortical slice as described by Wong et al., Proc. Natl. Acad. Sci. USA, 1986, 83, 7104. The apparent equilibrium constant ($K^b$) was calculated from the righthand shift in the NMDA or AMPA concentration-response curves produced by the compound under test. Of those compounds of the accompanying Examples which were tested, all were found to possess a $K^b$ value in response to NMDA of below 150 μM.

Binding Studies

The ability of test compounds to displace $^3$H-L-689,560 (trans-2-carboxy-5,7-dichloro-4-phenylaminocarbony-lamino-1,2,3,4-tetrahydroquinoline) binding to the strychnine-insensitive glycine site present on the NMDA receptor of rat forebrain membranes was determined by the method of Grimwood et al., *Proceedings of The British Pharmacological Society*, July 1991, Abstract C78. The concentration of the compounds of the accompanying Examples required to displace 50% of the specific binding ($IC_{50}$) is below 50 μM in each case.

EXAMPLE 1

4-Amino-7-chloro-3-(2-methoxyphenyl)-2(1H)-quinolone

5-Chloro-methyl anthranilate (20 g) and 300 ml of methanol saturated with ammonia were heated in an autoclave for 3 days at 150° C. and the solvent was allowed to evaporate for 14 h. The solid residue was triturated with diethyl ether and filtered. The brown solid obtained was suspended in 1N NaOH, subjected to ultrasound and filtered to afford 1.95 g of pure amide.

A solution of the amide (1.95 g) in tetrahydrofuran (150 ml) was stirred at 0° C. under a nitrogen atmosphere and was treated with anhydrous triethylamine (6.95 ml) followed by a solution of trifluoroacetic anhydride (4.3 ml) in tetrahydrofuran. The reaction mixture was stirred for 30 mins then partitioned between water and diethyl ether.

The organic phase was separated, the solvent was removed in vacuo and the residue was dissolved in 200 ml methanol-water (1:1) containing potassium carbonate (15 g). The reaction mixture was heated at 70° C. for 24 hrs, cooled, extracted into ethyl acetate, washed with water (3×) and brine (1×), dried (MgSO$_4$) and the solvent was removed under vacuum to give 5-chloroanthranilonitrile.

o-Methoxyphenyl acetyl chloride (0.8 g) and the product from above (0.6 g) were heated under reflux in dichloromethane (50 ml) for 14 h. The solvent was removed in vacuo and the residue was suspended in methanol and filtered to give the amide.

A solution of the amide (0.9 g) in DMF (50 ml) was treated with sodium hydride (1.2 g of 80% disp. in oil) and the reaction was heated at 100° C. for 1.5 h. The cooled reaction mixture was partitioned between ethyl acetate-water, and the organic phase was separated and washed with water (2×), brine (1×) and dried (MgSO$_4$). The solvent was removed and the residue was purified by preparative HPLC to give the title compound (0.1 g); mp 284°–286° C.; Found: C, 60.26; H, 4.35; N, 9.02; $C_{16}H_{13}N_2O_2Cl$. 1.0H$_2$O requires C, 60.29; H, 4.74; N, 8.79%. δ (360 MHz, DMSO-d$_6$) 3.70 (3H, s, ArOCH$_3$), 5.73 (2H, s, NH$_2$), 6.81–7.69 (6H, m, aromatics), 8.00 (1H, d, J=8.7 Hz, 5-H), 11.01 (1H, s, NHCO). m/z (CI$^+$) 301 (M+1).

EXAMPLE 2

4-Amino-7-chloro-3-phenyl-2(1H)-quinolone

5-Chloroanthranilonitrile (an Intermediate in Example 1) (0.9 g, 5.9 mmol) and phenylacetyl chloride were reacted in a similar manner to that described in Example 1 to give the title compound (0.87 g); mp 337°–338° C. (MeOH, DMF, H$_2$O). Found: C, 66.10; H, 4.25; N, 10.35. $C_{15}H_{11}ClN_2O$ requires C, 66.55; H, 4.10; N, 10.38%; δ (360 MHz, DMSO-d$_6$) 5.96 (2H, br s, NH$_2$), 7.14–8.04 (8H, m, aromatics), 11.10 (1H, br s, NH); m/z (EI) 270 (M$^+$).

EXAMPLE 3

4-Amino-7-chloro-3-(3-phenoxyphenyl)-2(1H)-quinolone

5-Chloro anthranilonitrile (0.9 g, 5.9 mmol) and 3-phenoxyphenyl acetic acid were reacted in a manner similar to that described in Example 1 to give the title compound (0.31 g); mp 196°–197° C. (dichloromethane); δ (360 MHz, DMSO-d$_6$) 6.09 (2H, br s, NH$_2$), 6.70–8.05 (12H, m, aromatics), 11.06 (1H, br s, NH); m/z (CI$^{31}$) 362 (M$^+$).

EXAMPLE 4

7-Chloro-4-methanesulphonamido-3-phenyl-2(1H)-quinolone

A solution of 4-amino-7-chloro-3-phenyl-2(1H)-quinolone (0.55 g, 2 mmol) (Example 2) and potassium (bistrimethylsilyl) amide (4 ml, 0.5M solution in toluene) in 50 ml tetrahydrofuran were stirred for 10 mins prior to the addition of tert-butyldimethylsilyl trifluoromethanesulfonate (6.1 ml). After a further 10 mins a further portion of potassium(bistrimethylsilyl)amide (6.1 ml) was added followed after 10 mins by methanesulfonyl chloride (0.48 ml). The solvent was removed in vacuo after one hour and the residue was suspended in 5N HCl (30 ml), and treated with ultrasound for 5 mins before being filtered. The solid was suspended in 1N NaOH and re-exposed to ultrasound then filtered to give the title compound (0.077 g); mp 222°–224° C. (DMF-water-diethyl ether); δ (360 MHz, DMSO-d$_6$) 2.17 (3H, s, CH$_3$), 7.34–7.67 (8H, m, aromatics), 9.60 (1H, br s, NHSO$_2$), 12.16 (1H, br s, NHCO); m/z (EI) 348 (M$^+$).

EXAMPLE 5

7-Chloro-4-phenylsulphonamido-3-phenyl-2(1H)-quinolone

Benzene sulphonylchloride (0.94 ml) and 4-amino-7-chloro-3-phenyl-2(1H)-quinolone (1 g) (Example 2) were reacted in a similar manner to that as described in Example 4. An additional step was required to remove the tert butyldimethylsilyl protecting group using methanolic-HCl for 20 mins to afford the title compound (0.050 g); mp 268° C. (ethanol); δ (360 MHz, DMSO-d$_6$) 7.14 (6H, m, aromatics), 7.32 (5H, m, aromatics), 7.49 (1H, m, aromatics), 7.67 (1H, d, J =8.7 Hz, 5H), 10.02 (1H, br s, 4NH), 12.15 (1H, br s, 1NH); m/z 410 (M$^+$).

EXAMPLE 6

4-Acetamido-7-chloro-3-phenyl-2(1H)-quinolone

A solution of 4-amino-7-chloro-3-phenyl-2(1H)-quinolone (Example 2) (0.3 g) in tetrahydrofuran (30 ml) was treated with sodium hydride (0.2 g, 80% disp. in oil). After 1 h, acetyl chloride (0.7 ml) was added and the reaction mixture was stirred for 2 h at room temperature then heated under reflux for 14 h. The reaction was partitioned between water and ethyl acetate. The organic phase was dried (MgSO$_4$) and the solvent was removed in vacuo. The residue was suspended in 1N NaOH, and placed in an ultrasound bath for 5 mins. The aqueous phase was extracted with diethyl ether, acidified to pill and the precipitate produced was collected by filtration to give the title compound (0.080 g); mp 275°–277° C. (DMF-water). Found: C, 58.39; H, 4.83; N, 8.02. $C_{17}H_{13}ClN_2O_2.2H_2O$ requires C, 58.54; H, 4.91; N, 8.03%; δ (360 MHz, DMSO-d$_6$) 1.88 (3H, s, CH$_3$CO), 7.22–7.58 (8H, m, aromatics), 9.69 (1H, br s, NH), 12.06 (1H, br s, NH); m/z (EI) 312 (M$^+$).

EXAMPLE 7

4-Carboxycarbonylamino-7-chloro-3-phenyl-2(1H)-quinolone

4-Amino-7-chloro-3-phenyl-2(1H)-quinolone (Example 2) (0.3 g) and ethyl oxalyl chloride (1.1 ml) were reacted in a similar manner to that described in Example 6 to give the title compound; mp 240° C. decomposed; Found: C, 57.70; H, 3.46; N, 7.93.$C_{17}H_{11}N_2O_4Cl.0.5H_2O$ requires C, 58.05; H, 3.44; N, 7.96%. δ (360 MHz, DMSO) 7.25–7.41 (7H, m, aromatics), 7.59 (1H, d, J=8.7 Hz, 5-H), 10.63 (1H, s, NHCOCO$_2$H), 12.20 (1H, s, NH); m/z (CI$^+$) 342 (M+1).

EXAMPLE 8

7-Chloro-4-methoxycarbonylcarbonylamino-3-phenyl-2(1H)quinolone

The product from Example 7 (0.34 g) was treated with saturated methanolic hydrogen chloride at room temperature for 14 h. The solvent was removed in vacuo and the residue was azeotroped with toluene (2x), then purified by chromatography (30 to 100% ethyl acetate-petrol eluent). This was followed by preparative HPLC to give the title compound (0.1 g); mp 240° C. decorap (methanol-water); Found: C, 57.77; H, 3.78; N, 6.98; $C_{18}H_{13}N_2O_4Cl.1.1H_2O$ requires C, 57.41; H, 4.07; N, 7.44%. δ (360 MHz, DMSO-d$_6$) 3.77 (3H, s, CO$_2$CH$_3$), 7.25–7.42 (7H, m, aromatics), 7.65 (1H, d, J=8.7 Hz, 6-H), 12.20 (1H, s, NH). m/z (CI$^+$) 357 (M+1).

EXAMPLE 9

4-Carboxymethylcarbonylamino-7-chloro-3-phenyl-2(1H)quinolone

A solution of 4-amino-7-chloro-3-phenyl-2(1H)-quinolone (Example 2) (0.5 g) in 50 ml tetrahydrofuran was stirred under an atmosphere of nitrogen and treated with sodium hydride (0.3 g, 80% disp. in mineral oil). This was followed by the addition after 1 h of ethyl malonyl chloride (1.8 ml). The reaction mixture was heated at 60° C. for 14 h, cooled and partitioned between ethyl acetate and water. The organic phase was washed with water (2x) before the solvent was removed in vacuo. The residue was saponified using 4N sodium hydroxide lo (100 ml) and ultrasound. The solution was adjusted to pill using conc. HCl then extracted into ethyl acetate, dried (MgSO$_4$) and the solvent was removed in vacuo. The residue was purified by preparative HPLC followed by recrystallisation from DMF-water to give the title compound (50 mg); mp 260° C. decomposed; δ (360 MHz, DMSO) 3.22 (2H, s, CH$_2$CO$_2$H), 7.22–7.76 (7H, m, aromatics), 7.87 (1H, d, 5-H, J=8.4 Hz), 9.97 (1H, s, NHCOCH$_2$CO$_2$H), 12.13 (1H, s, NH). Found: C, 60.29; H, 3.83; N, 7.69. $C_{18}H_{13}N_2O_4Cl$ requires C, 60.60; H, 3.67; N, 7.85%.

EXAMPLE 10

4-(2-Dimethylaminoethylamino)-7-chloro-3-phenyl-2(1H)quinolone

7-Chloro-4-hydroxy-3-phenyl-2(1H)-quinolone (1 g) and N,N-dimethylethylenediamine (30 ml) were heated in a sealed tube at 180° C. for 10 days. The reaction mixture was concentrated in vacuo and partitioned between ethyl acetate and saturated potassium carbonate solution. The organic layer was separated, dried (Na$_2$SO$_4$) and the solvent was removed under vacuum. The residue was dissolved in HCl, washed with diethyl ether (2x), then basified with sodium hydroxide, extracted into ethyl acetate, dried (MgSO$_4$), and concentrated in vacuo, to give 0.248 g of the title compound; mp 230° C. (ethyl acetate); Found: C, 63.76; H, 5.64; N, 11.75.$C_{19}H_2O ClN_3O.0.9H_2O$ requires C, 63.37; H, 6.14; N, 11.76%. δ (360 MHz, DMSO-d$_6$) 1.94 (6H, s, (CH$_3$)$_2$N), 2.17 (2H, m, NCH$_2$CH$_2$N), 2.69 (2H, m, NCH$_2$CH$_2$N), 5.82 (1H, br s, NH), 7.17–7.95 (8H, m, aromatics), 11.23 (1H, br s, NH); m/z (CI$^+$) 341 (M$^+$).

EXAMPLE 11

4-(3-Dimethylaminopropylamino)-7-chloro-3-phenyl-2(1H)quinolone

7-Chloro-4-hydroxy-3-phenyl-2(1H)-quinolone (1 g) and 3-dimethylaminopropylamine (30 ml) were heated together in a similar manner to that described for Example 10 to give the crude product, which was suspended in a mixture of 1:1 ethyl acetate and 1N HCl and filtered. The aqueous phase was basified to pH14 with sodium hydroxide and then extracted into ethyl acetate. The organic layer was dried (MgSO$_4$) and the solvent was removed to give the title compound (0.090 g); mp 177°–179° C. (diethyl ether). Found: C, 67.27; H, 6.22; N, 11.61. $C_{20}H_{22}ClN_3O$ requires C, 67.50; H, 6.23; N, 11.81%; δ (360 MHz, DMSO-d$_6$) 1.38 (2H, m, NCH$_2$CH$_2$CH$_2$N(CH$_3$)$_2$), 1.98 (2H, m, NCH$_2$CH$_2$CH$_2$N(CH$_3$)$_2$), 2.04 (6H, s, N(CH$_3$)$_2$), 2.58 (2H, m, NCH$_2$CH$_2$CH$_2$N(CH$_3$)$_2$), 6.58 (1H, m, NHCH$_2$CH$_2$CH$_2$N), 7.19–7.94 (8H, m, aromatics), 11.15 (1H, br s, NHCO); m/z (CI$^-$) 355 (M$^+$).

EXAMPLE 12

4-Benzylamino-7-chloro-3-phenyl-2(1H)-quinolone

7-Chloro-4-hydroxy-3-phenyl-2(1H)-quinolone (0.5 g) and benzylamine (20 ml) was heated under reflux for 24 h. The reaction was concentrated under high vacuum and the residue was triturated with diethyl ether and filtered. The filtrate was evaporated and purified by chromatography (25% ethyl acetate-dichloromethane eluent) to give the title compound as a white solid (0.045 g); mp 179° C. (diethyl ether). Found: C, 72.63; H, 4.45; N, 7.65. $C_{22}H_{17}ClN_2O.0.1H_2O$ requires C, 72.87; H, 4.78; o N, 7.72%; δ (360 MHz, DMSO-d$_6$) 3.81 (2H, d, J=4.8 Hz, PhCH$_2$NH), 8.67 (1H, t, J=4.8 Hz, PhCH$_2$NH), 6.85 (2H, d, J=6.5 Hz, ortho aromatics), 7.10–7.33 (11H, m, aromatics), 8.16 (1H, d, J=8.8 Hz, 5-H), 11.23 (1H, br s, NH); m/z (EI) 360 (M$^+$).

EXAMPLE 13

7-Chloro-4-(prop-2-en)oxy-3-phenyl-2(1H)-quinolone

7-Chloro-4-hydroxy-3-phenyl-2(1H)-quinolone (0.24 g, 8.8 mmol) and allylbromide (0.0765 ml) were stirred with sodium hydrogen carbonate (0.743 g) in DMF (10 ml) for 40 h. A further 0.5 equivalents of allyl bromide was added after 18 h. Water (100 ml) was added to the reaction mixture and the solid lo produced was collected by filtration. Trituration with methanol gave the title compound (0.090 g); mp 192°–193° C. (methanol). Found: C, 68.73; H, 4.59; N, 4.48. C$_{18}$H$_{14}$ClNO$_2$.0.2H$_2$O requires C, 68.55; H, 4.60; N, 4.44%; δ (360 MHz, DMSO-d$_6$) 4.06 (2H, d, J=5.8 Hz, OCH$_2$CH=CH$_2$), 5.12 (2H, m, OCH$_2$CH=CH$_2$), 5.76 (1H, m, OCH$_2$CH=CH$_2$), 7.25–7.83 (8H, m, aromatics), 11.90 (1H, br, s, NH); m/z (CI$^-$) 311 (M$^+$).

EXAMPLE 14

7-Chloro-4-methoxycarbonylmethoxy-3-phenyl-2(1H)-quinolone

A solution of 7-chloro-4-hydroxy-3-phenyl-2(1H)-quinolone (0.5 g) in DMF was stirred for 14 h with methyl bromoacetate (206 µl) and sodium bicarbonate (1.55 g). The reaction mixture was then partitioned between water and ethyl acetate. The aqueous phase was extracted with two further portions of ethyl acetate. The combined organic phases were washed with brine (3×), dried (MgSO$_4$) and the solvent was removed in vacuo to give the crude product which was recrystallised from ethyl acetate-hexane to give the title compound, 208 mg; mp 188°–191° C. (ethyl acetate-hexanes); Found: C, 63.27; H, 4.24; N, 4.07. C$_{18}$H$_{14}$ClNO$_4$ requires C, 62.89; H, 4.11; N, 4.07%; δ (360 MHz, DMSO-d$_6$) 3.55 (3H, s, CO$_2$CH$_3$), 4.19 (2H, s, CH$_2$CO$_2$), 7.28 (1H, dd, J=2.6, 8.7 Hz, 6-H), 7.35–7.40 (6H, m, aromatics), 8.01 (1H, d, J=8.7 Hz, 5-H), 11.92 (1H, s, NH); m/z CI$^+$344 (M$^+$).

EXAMPLE 15

4-Carboxymethoxy-7-chloro-3-phenyl-2(1H)-quinolone

A solution of 4-methoxycarbonylmethoxy-7-chloro-3-phenyl-2(1H)-quinolone (Example 14) (0.13 g) in 50 ml tetrahydrofuran was stirred at room temperature for 30 mins with lithium hydroxide (18.2ml, 0.5M solution). The solvent was removed in vacuo and the residue was dissolved in water and acidified to pH1 (1 N HCl). The precipitate was collected by filtration to give the title compound, 23 mg; mp 269°–272° C. (propan-2-ol then DMF-water); Found: C, 61.63; H, 3.61; N, 4.60.C$_{17}$H$_{12}$NO$_4$Cl requires C, 61.92; H, 3.69; N, 4.25%. δ (360 MHz, DMSO-d$_6$) 4.05 (2H, s, OCH$_2$), 7.29 (1H, dd, J=2.7, 8.7 Hz, 6-H), 7.35–7.47 (6H, m, Ar +8-H), 8.07 (1H, d, J=8.7 Hz, 5-H), 11.68 (1H, s, NH). m/z (CI$^-$) 328 (M-1).

EXAMPLE 16

4-Methoxycarbonylmethyl-7-chloro-3-phenyl-2(1H)quinolone

A solution of methyl 3-(2-amino-4-chloro)-phenyl prop-2-enoate (4 g, 19 mmol) and phenacetylchloride (5 ml, 38 mmol) in dichloromethane (100 ml) was heated under reflux for 14 h. The solvent was removed in vacuo, and the residue was azeotroped with methanol (100 ml). Trituration with methanol gave an intermediate amide; δ (360 MHz, DMSO-d$_6$) 3.73 (3H, s, CO$_2$CH$_3$), 6.60 (1H, d, J=15.9 Hz, CH$_A$=CH$_B$ CO$_2$CH$_3$), 7.24 7.38 (6H, m, aromatics+H-4), 7.55 (1H, d, J=2.1 Hz, H-6), 7.76 (1H, d, J=15.9 Hz, CH$_A$=CH$_B$CO$_2$CH$_3$), 7.85 (1H, d, J=8.6 Hz, H-3).

A solution of this amide (0.5 g, 1.5 mmol) in anhydrous tetrahydrofuran was cooled to −78° C. under a nitrogen atmosphere, and was treated with potassium bis(trimethylsilyl)amide (3.64 ml, 0.5M solution) via dropwise addition. After 10 mins t-butyldimethylsilyl trifluoromethanesulfonate (0.418 ml) was added and the reaction mixture was stirred for a further 45 mins prior to the addition of a further 1.2 equivalents of potassium bis(trimethylsilyl) amide. A solution of phenyl selenylchloride (0.316 g) in tetrahydrofuran (10 ml) was added after 10 mins. The reaction mixture was allowed to stir at −78° C. for 30 mins and then at room temperature for 14 h.

The reaction mixture was partitioned between ethyl acetate and saturated aqueous ammonium chloride. The aqueous phase was extracted with two further portions of ethyl acetate. The combined organic phases were washed with saturated aqueous brine, dried (MgSO$_4$) and all the solvent was removed in vacuo. The residue was purified by chromatography (15% ethyl acetate-hexane as eluent). The purified selenide was dissolved in 20 ml methanol-water (7:1) and was treated with sodium periodate (245 mg) for one hour. The precipitate was collected by filtration and purified by chromatography (30–50% ethyl acetate-hexane eluent) and preparative HPLC (40% acetonitrile-water eluent) to give the title compound (0.021 g); mp 227° C.; Found: C, 63.95; H, 4.34; N, 4.13. C$_{18}$H$_{14}$ClNO$_3$+0.5H$_2$O requires C, 64.19; H, 4.49; N, 4.16%. δ (360 MHz, DMSO-d$_6$) 3.58 (3H, s, methyl ester), 3.75 (2H, s, CH$_2$CO$_2$CH$_3$), 7.18 (2H, m, H-8+aromatics), 7.26 (1H, dd, J=2.1 and 8.7 Hz, H-6), 7.42 (4H, m, aromatics), 7.69 (1H, d, J=8.7 Hz, H-5), 12.07 (1H, s, NH); m/z (EI$^+$) 327 (M$^+$).

EXAMPLE 17

4-Carboxymethyl-7-chloro-3-phenyl-2(1H)-quinolone

A suspension of methoxycarbonylmethyl-7-chloro-3-phenyl-2(1H)-quinolone (0.12 g) (Example 16) in 50% methanol-water (20 ml) was heated under reflux for one hour with sodium hydroxide (200 mg). The methanol was removed under vacuum, and the residue was extracted with three portions of diethyl ether. The aqueous phase was acidified (c.HCl) and extracted with three portions of ethyl acetate. The combined organic extracts were washed with brine, dried (MgSO$_4$) and the solvent was removed in vacuo, to give the title compound (0.05 g); mp 175° C. (ethanol); Found: C, 64.80; H, 4.23; N, 4.42. C$_{17}$H$_{12}$ClNO$_3$ requires C, 65.08; H, 3.86; N, 4.46%. δ (360 MHz, DMSO-d$_6$) 5.65 (2H, s, —CH$_2$CO$_2$H), 7.23 (2H, aromatics), 7.26 (1H, dd, J=2.1, 8.6 Hz, H-6), 7.41 (4H, m, aromatics), 7.69 (1H, d, J=8.6 Hz, H-5), 12.03 (1H, s, NH), 12.68 (1H, br s, CO$_2$H); m/z (CI$^+$) 313 (M$^+$).

EXAMPLE 18

4-Carboxy-7-chloro-3-phenyl-2(1H)-quinolone

A mixture of 4- and 6-chloroisatin (2.72 g), phenyl acetic acid (3.57 g) and sodium acetate (0.3 g) were heated at 220° C. for 1 h. Acetic acid (20 ml) was added to the hot reaction mixture, and the cooled solution was partitioned between saturated sodium carbonate and ethyl acetate. The aqueous phase was acidified to pH1 (c. HCl), and the precipitate was collected by filtration to give the title compound (60 mg); mp 258° C. (ethanol); (Found: C, 63.94; H, 3.32; N, 4.59. $C_{16}H_{10}Cl_1N_1O_3$ requires C, 64.12; H, 3.36; N, 4.67%); δ (360 MHz, DMSO-$d_6$) 7.30 (1H, dd, J=8.7, 2.1 Hz, H-6), 7.39 (6H, m, aromatics, H-8), 7.50 (1H, d, J=8.7 Hz, H-5), 12.2 (1H, s, NH), 14.0 (1H, br s, $CO_2H$); m/z=299 ($M^+$).

EXAMPLE 19

7-Chloro-3-(2-aminophenyl)-2(1H)-quinolone

A solution of oxalyl chloride (20 ml) in $CH_2Cl_2$ (300 ml) was added over 1 h to a solution of 2-nitrophenylacetic acid (27 g) in DMF (0.51). 2-Amino-4-chlorobenzylalcohol (9.4 g)in $CH_2Cl_2$ (200ml) was added and the reaction mixture was heated under reflux for 1 h. The cooled solution was washed with saturated lo sodium hydrogen carbonate, brine, dried (MgSO$_4$) and the solvent was removed in vacuo to leave a black solid which was recrystallised from ethyl acetate-hexane to leave 20.1 g of a brown solid.

This product was stirred with potassium carbonate (3 g) in methanol (300 ml) at room temperature for 14 h. The solvent was removed in vacuo and the residue was partitioned between water and ethyl acetate. The organic phase was washed with water, brine, dried (MgSO$_4$) and the solvent was removed in vacuo. The residue was recrystallised to give 7.8 g of the amide, mp 155°–157° C. (propan-2-ol).

The amide was dissolved in $CH_2Cl_2$ (100 ml) and stirred for 2 h with pyridinium chlorochromate (4 g), ethyl acetate was added, and the reaction mixture was filtered through silica. The solvent was removed and the residue was recrystallised from ethyl acetate to give 1.83 g of the aldehyde as white cubes.

The aldehyde was stirred with sodium methoxide (0.6 g) in methanol (100 ml) for 3 h. The reaction mixture was concentrated to a volume of 20 ml. Trifluroacetic acid was added and the solid was collected, washed with methanol, and dried to leave 1.48 g yellow solid.

The aromatic nitro compound (100 mg) was hydrogenated over PtO$_2$ (20 mg) at 50 psi in ethyl acetate (20 ml) for 90 mins. The reaction mixture was filtered and the solid was dissolved in hot methanol, the combined filtrates evaporated, and recrystallised to give the title compound as fine yellow needles. mp 287°–290° C. (methanol); (Found: C, 64.22; H, 4.49; N, 9.85. $C_{15}H_{11}N_2OCl+0.5H_2O$ requires C, 64.41; H, 4.32; N, 10.01%); δ (360 MHz, DMSO-$d_6$) 4.34 (2H, s, NH$_2$), 6.62 (1H, t, J=7.2 Hz, H-5'), 6.73 (1H, d, J=7.2 Hz, H-3'), 7.04 (1H, d, J=7.2 Hz, H-6'), 7.08 (1H, d, J=7.2 Hz, H-4 '), 7.24 (1H, dd, J=2.1 and 8.4 Hz, H-6), 7.57 (1H, d, J=2.1 Hz, H-8), 7.74 (1H, d, J=8.4 Hz, H-5), 7.92 (1H, s, H-4), 12.0 (1H, s, NH); m/z ($CI^+$, NH$_3$) 271 ($M^+$+H).

EXAMPLE 20

7-Chloro-3-(4-hydroxyphenyl)-2(1H)-quinolone

2-Amino-4-chlorobenzyl alcohol (4 g, 25.3 mol) and 4-methoxyphenyl acetic acid (14.0 g, 76.4 mmol) were reacted in a similar manner to that described in Example 19 to give 7-chloro- 3-(4-methoxyphenyl)-2(1H)-quinolone; mp 256°–257° C. (ethyl acetate).

A suspension of the above product (200 mg, 0.7 mmol) in $CH_2Cl_2$ (40 ml) was treated with boron tribromide (0.7 g, 2.8 mmol) at room temperature. A further equivalent of BBr$_3$ was added after 2 h and reaction was complete after 5 h. The reaction was washed with saturated sodium hydrogen carbonate, brine and the solvent was evaporated to give the title compound as white needles, mp 262° C. (from EtOAc); (Found: C, 65.57; H, 3.97; N, 5.11. $C_{15}H_{10}NO_2Cl+0.15H_2O$ requires: C, 66.31; H, 3.71; N, 5.15%); $δ_H$ (360 MHz, DMSO-$d_6$) 6.83 (2H, d, J=6.6 Hz, 3'-H), 7.21 (1H, dd, J=8.4, 2.0 Hz, 6'-H), 7.53 (1H, d, J=2.0 Hz, 8'-H), 7.63 (2H, d, J=6.6 Hz, 2'-H), 7.73 (1H, d, J=8.4 Hz, 5-H), 8.02 (1H, s, 4-H), 9.61 (1H, s, OH), 11.92 (1H, s, NH); m/z ($EI^+$) 271 ($M^+$).

EXAMPLES 21 & 22

7-Chloro-3-(2-methoxyphenyl)-2(1H)-quinolone and 7-Chloro-3-(2-hydroxyphenyl)-2(1H)-quinolone 2-Amino-4-chlorobenzyl alcohol (2 g, 12.86 mmol) and 2-methoxyphenylacetic acid (4.70 g, 28.3mol) were reacted in a similar manner as described in Example 19 to give 7-chloro-3-(2-methoxyphenyl)-2(1H)-quinolone as fine white needles mp 235°–236° C. (MeOH). (Found: C, 67.49; H, 4.22; N, 4.93. $C_{16}H_{12}ClNO_2$ requires C, 67.26; H, 4.23; N, 4.90%); $δ_H$ (360 MHz, $d_6$-DMSO) 3.73 (1H, s, CH$_3$) 6.97 (1H, dt, J=0.8 and 7.4 Hz, 5'-H) 7.08 (1H, d, J=8.3 Hz, 3'-H) 7.22 (1H, dd, J=8.4 and 2.1 Hz, 6-H) 2.27 (1H, dd, J=7.5 and 1.7 Hz, 6'-H) 7.34 (1H, d, J=1.8 Hz, 8-H) 7.37 (1H, dt, J=1.7 and 8.2 Hz, 4'-H) 7.70 (1H, d, J=8.4 Hz, 5-H) 7.87 (1H, s, 4-H) 11.87 (1H, br s, NH); m/z ($EI^+$) 285 ($M^+$). The quinolone (300 mg) and boron tribromide (3.15 ml, 1N solution in $CH_2Cl_2$) were reacted as described in Example 20 to give 286 mg of 7-chloro-3-(2-hydroxyphenyl)-2(1H)-quinolone as a yellow crystalline solid; mp 246°–248° C. (dec) (methanol). (Found: C, 66.43; H, 3.70; N, 5.17. $C_{15}H_{10}ClNO_2$ requires C, 66.31; H, 3.71; N, 5.15%); $δ_H$ (360 MHz, DMSO-$d_6$) 6.87 (1H, t, J=8.2 Hz, 5'-H), 6.90 (1H, d, J=7.8 Hz, 3'-H), 7.22 (1H, dt, J=1.7 and 7.8 Hz, 4'-H), 7.26 (1H, dd, J=8.4 and 2.1 Hz, 6-H), 7.31 (1H, dd, J=8.2 and 1.7 Hz, 6'-H), 7.39 (1H, d, J=2.1 Hz, 8-H), 7.77 (1H, d, J=8.4 Hz, 5-H), 8.03 (1H, s, 4-H), 9.56 (1H, br s, OH), 12.14 (1H, br s, NH); m/z ($EI^+$) 271 ($M^+$).

EXAMPLE 23

7-Chloro-3-(3-carboxyphenyl)-2(1H)-quinolone

A solution of methyl-3-hydroxyphenylacetate (3.32 g, 20 mmol) and Hünig's base (4.36 ml) in 100 ml dichloromethane at 0° C. was treated slowly with trifluoromethanesulphonic anhydride. The reaction was stirred for 0.5 h at 0° C. then 1.5 h at room temperature. The reaction was washed with water (50 ml), 10% citric acid (50 ml), sodium hydrogen carbonate (50 ml), dried (MgSO$_4$), treated with silica and solvent removed in vacuo to leave 5.92 g of the triflate as a pale yellow oil. δ (CDCl$_3$) 3.67 (2H, s, CH$_2$), 3.72 (3H, s, OMe), 7.18–7.23 (2H, m, 2-H and 4-H), 7.31 (1H, d, J=8.9 Hz, 6-H) and 7.39–7.43 (1H, m, 5-H).

The triflate (1.49 g) was mixed with triethylamine (1.4 ml), methanol (5 ml), DMF (10 ml), palladium acetate (40 mg) and 1,1'-bis(diphenylphosphine)ferrocene (221 mg) to give a brown solution. The reaction was purged with carbon monoxide for 5 mins and then heated to 60° C. under an atmosphere of carbon monoxide. Volatiles were removed in vacuo and the residue partitioned between brine and ethyl acetate. The organic extracts were washed with brine, 1N HCl, brine, dried (MgSO$_4$) and solvent removed in vacuo. The residue was chromatographed (15% to 25% ethyl acetate-petrol) to give the dimethyl ester of 3-(carboxy)phenyl acetic acid as an oil (0.87 g). δ (CDCl$_3$) 3.68 (2H, s, CH$_2$), 3.70 (3H, s, CH$_2$CO$_2$Me), 3.92 (3H, s, ArCO$_2$Me), 7.39–7.43 (1H, m, 5-H), 7.49 (1H, d, J=7.7 Hz, 6-H) and 7.94–7.96 (2H, m, 2-H and 4-H).

Dimethyl-3-carboxyphenyl acetic acid (870 mg) in 10 ml tetrahydrofuran was treated with lithium hydroxide (8.5 ml, 0.5M solution) at 0° C. After stirring at room temperature for 4 h, all solvent was evaporated, and the residue partitioned between saturated sodium hydrogen carbonate and ethyl acetate. The aqueous layer was separated, acidified (1N HCl) and extracted with dichloromethane (2×25 ml). The combined organic layers were dried (MgSO$_4$) and solvent removed to leave 3-(carboxymethyl)phenyl acetic acid, mp 96°–98° C.

To a solution of 4-chloro-2-nitrobenzyl alcohol (15 g, 100 mmol) in dry DMF (80 ml) was added imidazole (14.3 g) and tert-butyldimethylsilylchloride (16.6 g). The reaction was stirred for 14 h and partitioned between diethyl ether and water. The organic phase was dried (MgSO$_4$) and solvent removed to give the tert-butyldimethylsilyl protected alcohol. δ (250 MHz, CDCl$_3$) 0.0 (6H, s), 0.8 (9H, s), 4.95 (2H, s), 7.5 (1H, dd, J=4 and 8 Hz), 7.7 (1H, d, J=8 Hz), 7.77 (1H, d, J=4 Hz).

A solution of the protected alcohol (24 g) in ethyl acetate (400 ml) was hydrogenated over PtO$_2$ (2 g) at 50 psi over 3 h. The reaction was filtered, and solvent removed. The residue was purified by chromatography (10% ethyl acetate-petrol eluent) to give the t-butyldimethylsilyl protected 4-chloro-2-amino benzyl alcohol. δ (360 MHz, CDCl$_3$) 0.07 (6H, s), 0.91 (9H, s), 4.59 (2H, s), 6.6 (d, J=8 Hz), 6.94 (1H, d, J=8 Hz), 7.28 (1H, s).

Oxalyl chloride (1.40 ml) was added to a solution of 3-(carboxymethyl)-phenyl acetic acid (2.04 g) (from 3 above) in CH$_2$Cl$_2$ (30 ml) containing DMF (3 drops). The reaction was stirred for 2 h, evaporated and azeotroped with CCl$_4$ (2×20 ml). The residue was dissolved in CH$_2$Cl$_2$ (15 ml) and was added to a solution of the amine (3.26 g) (from 5 above) in pyridine (10 ml) and CH$_2$Cl$_2$ (75 ml) at 0° C. The reaction was stirred for 14 h, evaporated and then partitioned between ethyl acetate and water. The organic phase was separated and washed with 10% citric acid, brine, dried (MgSO$_4$) and evaporated. The residue was purified by chromatography (10–20% ethyl acetate-petrol eluent) to give the amide. δ (CDCl$_3$) –0.03 (3H, s, SiMe), –0.01 (3H, s, SiMe), 0.83 (9H, s, t-Bu), 3.71 (2H, s, —CH$_2$CO—), 3.89 (3H, s, OMe), 4.57 (2H, s, —CH$_2$O—), 6.96 (2H, s, ArH), 7.42 (1H, t, J=7.6 Hz, 5'-H), 7.52–7.55 (1H, m, ArH), 7.95–7.99 (2H, m, ArH), 8.25 (1H, s, ArH) and 8.86 (1H, br s, NH).

HF-pyridine (2 ml) was added to a solution of the amide (3.09 g) (from 6 above) in dichloromethane (25 ml) and pyridine (10 ml). The reaction was stirred for 2 h with a further 1 ml of HF-pyridine being added after 1.5 h. Solvent was removed in vacuo, the residue dissolved in ethyl acetate and washed with 1N HCl (3×), brine, dried (MgSO$_4$), treated with SiO$_2$ and evaporated. The benzyl alcohol was recrystallised from ethyl acetate-petroleum ether; δ (CDCl$_3$) 3.79 (2H, s, —CH$_2$CO), 3.93 (3H, s, OMe), 4.49 (2H, s, —CH$_2$OH), 6.98–7.03 (2H, m, ArH), 7.46 (1H, t, J=7.7 Hz, ArH), 7.55 (1H, d, J=7.6 Hz, ArH), 7.79 (1H, d, J=7.6 Hz, ArH), 8.04 (1H, s, ArH), 8.19 (1H, s, ArH) and 8.72 (1H, br s, NH).

The benzyl alcohol (1.65 g) was oxidised and cyclised in a similar manner as described in Example 19 to give the ester (1.2 g); mp 263°–265° C. (DMF-water).

The ester (280 mg) was saponified using methanol (15 ml) and sodium hydroxide (3 ml, 1N solution) at room temperature for 15 mins followed by heating to reflux for 0.5 h. Tetrahydrofuran (5 ml) was added and reflux continued for 2 h. Solvent was removed in vacuo and the residue was suspended in water, and adjusted to pH1 (1N HCl). The precipitate was collected, washed with water then methanol and dried to give the title compound; mp>330° C. (DMF-water). Found: C, 60.95; H, 3.92; N, 4.62. C$_{16}$H$_{10}$ClNO$_3$+ 0.9H$_2$O requires C, 60.83; H, 3.76; N, 4.43. δ (360 MHz, DMSO-d$_6$) 7.26 (1H, dd, J=8.4, 2.0 Hz, 6-H), 7.37 (1H, d, J=2.0 Hz, 8-H), 7.57 (1H, t, J=7.8 Hz, 5'-H), 7.80 (1H, d, J=8.4 Hz, 5-H), 7.95–8.01 (2H, m, 4'-H and 6'-H), 8.23 (1H, s, 4-H), 8.35 (1H, s, 2'-H) and 12.09 (1H, br s, NH).

EXAMPLE 24

7-Chloro-3-phenyl-4-[(2-oxo)propoxy]-2(1H)-quinolone

To a stirred suspension of 7-chloro-4-hydroxy-3-phenyl-2(1H)-quinolone (0.50 g 0.0018 mol), sodium hydrogen carbonate (1.55 g, 0.018 mol) and sodium iodide (0.20 g) in N,N-dimethylformamide (20 ml) was added chloroacetone (0.20 g, 0.0020 mol). The reaction was stirred for 24 h, then the product was precipitated by the addition of water (50 ml). The product was collected by filtration, washed with water (3×10 ml) and dried under vacuum at 60° C. Recrystallisation from ethyl acetate/60–80 petrol gave a white crystalline solid; yield=390 mg, mp=185°–186° C.; Found: C, 66.20; H, 4.33; N, 4.20; C$_{18}$H$_{14}$ClNO$_3$ requires C, 65.96; H, 4.31; N, 4.27. δ (360 MHz, DMSO-d$_6$), 1.84 (3H, s, CH$_3$CO), 4.26 (2H, s, CH$_2$), 7.26 (1H, dd, J=8.7 and 2.1 Hz, 6-H), 7.30–7.46 (6H, m, aromatics), 8.02 (1H, d, J=8.7 Hz, 5-H), 11.90(1H, s, br, NH). MS (CI) m/z=328 (MH)$^+$.

EXAMPLE 25

7-Chloro-3-phenyl-4-[(2-oximino)propoxy]-2(1H)-quinolone

The product from Example 24 (0.50 g, 0.0015 mol), hydroxylamine hydrochloride (0.21 g, 0.0031 mol) and 4 Å molecular sieves were suspended in pyridine (10 ml) and heated at 60° C. for 14 h. A further amount of hydroxylamine hydrochloride (0.42 g, 0.0062 mol) was added and the reaction mixture heated under reflux for a further 24 h. The reaction mixture was diluted with ethyl acetate (30 ml) and filtered through hiflo. The mixture was washed with 1N hydrochloric acid (100 ml), the acid layer was back extracted with ethyl acetate (2×20 ml) and the combined organic layers were washed consecutively with water (20 ml), saturated sodium hydrogen carbonate solution (20 ml) and brine (20 ml), then dried (MgSO$_4$), filtered, and concentrated in vacuo to give a white solid. This was recrystallised from ethanol/water to give a white crystalline solid; yield=278 mg. Mp=196°–198° C. Found: C, 62.93; H, 4.37; N, 8.10. C$_{18}$H$_{15}$ClN$_2$O$_3$ requires C, 63.07; H, 4.41; N, 8.17. δ (360 MHz, DMSO-d$_6$), 1.60 (3H, s, CH$_3$), 4.06 (2H, s, OCH$_2$), 7.28 (1H, dd, J=8.6 and 2.1 Hz, 6-H), 7.32–7.48 (6H, m, aromatics), 7.78 (1H, d, J=8.7 Hz, 5-H), 10.88 (1H, s, NOH), 11.92 (1H, s, br, NH). MS (CI) m/z=343 [MH]$^+$.

EXAMPLE 26

7-Chloro-3-phenyl-4-(prop-2-ynyloxy)-2(1H)-quinolone

This was prepared as for Example 24 but using propargyl bromide (0.48 g, 0.0044 mol) and 7-chloro-4-hydroxy-3-phenyl-2(1H)-quinolone (0.50 g, 0.0018 mol) and recrystallising the product from ethanol/water; yield=210 mg as a white crystalline solid, mp=183°–185° C. Found: C, 69.21; H, 3.68; N, 4.34. $C_{18}H_{12}ClNO_2+0.1\ H_2O$ requires C, 69.39; H, 3.95; N, 4.50. δ (360 MHz, DMSO-$d_6$), 3.50 (1H, t, J=2.3 Hz, CCH), 4.26 (2H, d, J=2.5 Hz, OCH$_2$C), 7.28 (1H, dd, J=8.5 and 1.9 Hz, H$_6$), 7.32–7.48 (6H, m, aromatics), 7.86 (1H, d, J=8.6 Hz, H$_5$), 11.96 (1H, s, br, NH). MS (CI) m/z=310 [MH]$^+$.

EXAMPLE 27

7-Chloro-3-phenyl-4-[2-(O-methyl)oximino]propyloxy-2(1H)-quinolinone

The product from Example 24 (0.50 g, 0.0015 mol), O-methylhydroxylamine hydrochloride (0.25 g, 0.0031 mol) and 4 Å molecular sieves were suspended in pyridine (10 ml) and heated at 60° C. for 14 h. The reaction mixture was cooled, the solvent was removed in vacuo and the resulting solid was redissolved in ethyl acetate (200 ml). The solution was washed with 1N hydrochloric acid (50 ml), the acid layer was back extracted with ethyl acetate (2×25 ml) and the combined organic layers were washed consecutively with water (20 ml), saturated sodium carbonate solution (20 ml), and brine (20 ml) and then dried (MgSO$_4$), filtered, and the solvents removed in vacuo to give a white solid. This was recrystallised from ethanol/water to give the desired product as white needles; yield=185 mg. Mp=192°–195° C. Found: C, 63.52; H, 4.83; N, 7.66. $C_{19}H_{17}ClN_2O_3$. 0.1 $H_2O$ requires C, 63.63; H, 4.83; N, 7.81. δ (360 MHz, DMSO-$d_6$) 1.58 (3H, s, CCH$_3$), 3.71 (3H, s, NOCH$_3$), 4.06 (2H, s, OCH$_2$), 7.28 (1H, dd, J=8.7 and 2.1 Hz, 6-H), 7.32–7.48 (6H, m aromatics), 7.80 (1H, d, J=8.6 Hz, 5-H), 11.91 (1H, s, br, NH). MS (CI) m/z=355 [MH]$^+$.

EXAMPLE 28

7-Chloro-4-methoxycarbonylmethoxy-3-(3-phenoxy)phenyl-2(1H)-quinolone

To a solution of 7-chloro-4-hydroxy-3-(3-phenoxy)phenyl-2(1H)-quinolone (1.5 g) in DMF (50 ml) under nitrogen at room temperature, was added NaHCO$_3$ (3.5 g) followed by methyl bromoacetate (0.57 ml). The reaction mixture was stirred at room temperature for 16 h, then poured into water (110 ml) and extracted with ethyl acetate (2×100 ml). The combined organic layers were washed with brine (2×75 ml), dried (MgSO$_4$), filtered and the solvent was removed in vacuo to leave a solid residue. Recrystallisation from an ethyl acetate, petrol (60–80) mixture and then recrystallisation from dichloromethane, petrol (60–80) mix gave the title compound (0.36 g); mp 190°–192° C. Found: C, 65.93; H, 4.33; N, 3.31; $C_{24}H_{18}NO_5Cl$ requires C, 66.14; H, 4.16; N, 3.21%. δ (360 MHz, DMSO-$d_6$) 3.59 (3H, s, OCH$_2$CO$_2$CH$_3$), 4.30 (2H, s, OCH$_2$CO$_2$CH$_3$), 7.03–7.48 (11H, m, Ph+Ph+6-H+8-H), 7.99 (1H, d, J=8.65 Hz, 5-H), 11.91 (1H, bs, NH). m/z (CI$^+$), 436, (M+1).

EXAMPLE 29

4-Carboxymethoxy-7-chloro-3-(3-phenoxy)phenyl-2(1H)-quinolone

To a solution of 7-chloro-4-methoxycarbonylmethyloxy-3-(3-phenoxy)- 2(1H)-quinolone (Example 28, 0.24 g) in tetrahydrofuran (50 ml) at room temperature, was added a 0.5N solution of lithium hydroxide (26.45 ml). The reaction mixture was stirred at room temperature for 1 h, then the organic solvent was removed in vacuo. The aqueous residue was acidified to pH 1 using concentrated HCl and the emerging precipitate was collected by filtration and dried at 50° C. for 2 h to give the title compound (0.05 g). Mp 246°–249° C. Found: C, 62.61; H, 3.72; N, 3.30; $C_{23}H_{16}NO_5Cl.H_2O$ requires C, 62.80; H, 4.12; N, 3.19%. δ (360 MHz, DMSO-$d_6$) 4.18 (2H, s, OCH$_2$CO$_2$H), 7.04–7.48 (11H, m, Ph+Ph+6-H+8-H), 8.02 (1H, d, J=8.55 Hz, 5-H), 11.93 (1H, bs, NH). m/z (FAB$^+$), 422, (m+1).

EXAMPLE 30

7-Chloro-4-cyanomethoxy-3-phenyl-2(1H)-quinolone

To a solution of 7-chloro-4-hydroxy-3-phenyl-2(1H)-quinolone (0.50 g, 1.84 mmol) in dimethyl formamide (50 ml) under nitrogen at room temperature, was added sodium hydrogen carbonate (1.50 g) followed by bromoacetonitrile (1.9 ml). The reaction mixture was stirred at room temperature for 16 h, then poured into water and extracted with ethyl acetate (3×50 ml). The combined organic layers were washed with water (2×50 ml), dried (MgSO$_4$), filtered and the solvent was removed in vacuo to leave an oily residue. Trituration with diethyl ether, followed by recrystallisation from an ethyl acetate, petrol (60–80) mixture, gave the title compound as a white solid (0.15 g). Mp 209°–211° C. Found: C, 65.60; H, 3.74; N, 8.75; $C_{17}H_{11}N_2O_2Cl$ requires C, 65.71; H, 3.57; N, 9.02%. δ (360 MHz, DMSO-$d_6$) 4.59 (2H, s, OCH$_2$CN), 7.31 (1H, dd, J=8.63 Hz, J=2.10 Hz, 6-H), 7.40–7.49 (6H, m, Ph+8-H), 7.83 (1H, d, J=88.63 Hz, 5-H), 12.10 (1H, bs, NH). m/z (CI$^+$), 311, (M+1).

EXAMPLE 31

7-Chloro-4-cyanomethoxy-3-(3-phenoxy)phenyl-2(1H)-quinolone

To a solution of 7-chloro-4-hydroxy-3-(3-phenoxy)phenyl-2(1H)-quinolone (0.75 g, 2.06 mmol) in dimethyl formamide (50 ml) under nitrogen at room temperature, was added sodium hydrogen carbonate (1.80 g) followed by bromoacetonitrile (0.21 ml). The reaction mixture was stirred at room temperature for 16 h, then poured into water (100 ml) and the emerging precipitate was filtered. Recrystallisation from an EtOAc, petrol (60–80) mixture gave the title compound in 16% yield (0.13 g). Mp 218°–220° C. Found: C, 68.97; H, 3.67; N, 6.88; $C_{23}H_{15}N_2O_3Cl$ requires C, 68.58; H, 3.75; N, 6.95%. δ (360 MHz, DMSO-$d_6$) 4.70 (2H, s, OCH$_2$CN), 7.08–7.51 (11H, m, Ph+Ph+6-H+8-H), 7.82 (1H, d, J=8.67 Hz, 5-H), 12.10 (1H, bs, NH). m/z (CI$^+$), 403, (M+1).

EXAMPLE 32

7-Chloro-4-N,N-dimethylaminocarbonylmethoxy-3-phenyl-2(1H)quinolone

To a saturated solution of dimethylamine in methanol (200 ml) at 0° C. was added 7-chloro-4-methoxycarbonyl methoxy-3-phenyl-2(1H)-quinolone (Example 28, 0.30 g). The reaction mixture was sealed and left for 5 days. Removal of the solvent in vacuo and recrystallisation from an EtOAc, MeOH mixture gave the title compound (0.21 g). Mp 232°–234° C. Found: C, 64.38; H, 4.92; N, 7.78; $C_{19}H_{17}N_2O_3Cl$ requires C, 63.96; H, 4.80; N, 7.85%. δ (360 MHz, DMSO-$d_6$) 2.42 (3H, s, OCH$_2$NCH$_3$), 2.69 (3H, s, OCH$_2$NCH$_3$), 4.30 (2H, s, OCH$_2$N(CH$_3$)$_2$), 7.24 (1H, dd, J=8.62 Hz, J=2.05 Hz, 6-H), 7.32–7.47 (6H, m, Ph+8-H), 7.98 (1H, d, J=8.62 Hz, 5-H), 11.83 (1H, s, NH). m/z (CI$^+$), 403, (m+1).

EXAMPLE 33

7-Chloro-4-(2-N,N dimethylaminoethyl)oxy-3-phenyl-2(1H)quinolone

A. 4-(prop-2-enyloxy)-7-chloro-3-phenyl-2(1H)-quinolone

To a solution of 7-chloro-4-hydroxy-3-phenyl-2(1H)-quinolone (5.00 g) in dimethyl formamide (150 ml) under nitrogen at room temperature, was added sodium hydrogen carbonate (15.47 g). The reaction mixture was stirred at room temperature for 30 mins then allyl bromide (2.39 ml) was added, and stirring continued for a further 36 h at room temperature. The mixture was poured into water (200 ml) and the emerging precipitate was filtered and triturated with boiling methanol to give the desired compound as a beige solid in 50% yield. $^1$H NMR (360 MHz, DMSO-$d_6$) δ 4.04 (2H, dd, J=6.45 Hz, J=1.84 Hz, OCH$_2$CHCH$_2$), 5.08 (2H, m, OCH$_2$CHCH$_2$), 5.88 (1H, m, OCH$_2$CHCH$_2$), 7.23 (1H, dd, J=12.45 Hz, J=3.00 Hz, 6-H), 7.36 (6H, m, Ph+8-H), 7.81 (1H, d, J=12.45 Hz, 5-H), 11.94 (1H, bs, NH).

B. 7-Chloro-4-(2-N,N dimethylaminoethyl)oxy-3-phenyl--2(1H)-quinolone

A solution of 4-(prop-2-enyloxy)-7-chloro-3-phenyl-2(1H)-quinolone (0.30 g) in dichloromethane (50 ml) at −78° C. had ozone passed through for 15 mins (solution turned to an electric blue colour). The reaction mixture was allowed to warm to room temperature and stirred for 1 h before adding dimethyl sulfide (0.50 ml). After stirring for a further 30 mins the solvent was removed under vacuum to leave a solid residue. The residue was dissolved in methanol (50 ml) and dimethylamine hydrochloride (0.40 g) and sodium cyanoborohydride (0.06 g) were added. The pH of the solution was measured and observed to be 4. The reaction was stirred at room temperature for 16 h, then the mixture was basified to pH 9 using 1N sodium hydroxide and the solution was extracted with ethyl acetate (3×50 ml). The combined organic layers were extracted with 1N HCl (1×100 ml) and the aqueous layer washed with ethyl acetate (2×50 ml), before being basified to pH 9 using 1N sodium hydroxide and re-extracted with EtOAc (3×50 ml). The combined organic layers were dried (MgSO$_4$), filtered and the solvent was removed in vacuo to leave a solid residue. Recrystallisation from ethyl acetate, then an ethyl acetate petrol (60–80) mix, gave the title compound in a 10% yield (0.03 g). Mp 185°–187° C. Found: C, 66.31; H, 5.95; N, 7.46; $C_{19}H_{19}N_2O_2Cl$ 0.1$C_6H_{14}$ 0.6$H_2O$ requires C, 65.97; H, 5.93; N, 7.85%. δ (360 MHz, DMSO-$d_6$) 2.00 (6H, s, 2×NCH$_3$), 2.33 (2H, t, J=5.78 Hz, OCH$_2$CH$_2$N(CH$_3$)$_2$), 3.55 (2H, t, J=5.78 Hz, OCH$_2$CH$_2$N(CH$_3$)$_2$), 7.24 (1H, dd, J=9.31 Hz, J=2.10 Hz, 6-H), 7.35–7.46 (6H, m, Ph+8-H), 7.91 (1H, d, J=9.31 Hz, 5-H), 11.67 (1H, bs, NH). m/z (CI$^+$), 343, (m+1).

EXAMPLE 34

4-Aminocarbonylmethoxy-7-chloro-3-phenyl-2(1H)-quinolone

To a solution of 4-carboxymethoxy-7-chloro-3-phenyl--2(1H)-quinolone (0.93 g Example 15) in tetrahydrofuran (50 ml) under nitrogen at room temperature, was added triethylamine (1.90 ml), ammonium acetate (0.50 g), 1-hydroxybenzotriazole (0.60 g) and 1-(3 dimethylaminopropyl)-3-ethyl carbodiimide (0.90 g). The reaction mixture was stirred at room temperature for 3 days, then poured into water (100 ml) and extracted with ethyl acetate (3×50 ml). The combined organic layers were washed with 1N citric acid (1×75 ml), water (1×75 ml), saturated sodium hydrogen carbonate (1×75 ml) and brine (1×75 ml), then dried (MgSO$_4$), filtered and the solvent was removed in vacuo to leave a solid residue. Recrystallisation from MeOH gave the title compound (0.29 g). Mp 262°–264° C. Found: C, 66.31; H, 5.95; N, 7.46; $C_{19}H_{19}N_2O_2Cl$ 0.1$C_6H_{14}$ 0.6$H_2O$ requires C, 65.97; H, 5.93; N, 7.85%. δ (360 MHz, DMSO-$d_6$) 3.91 (2H, s, OCH$_2$CONH$_2$), 7.25–7.45 (9H, m, Ph+6H+8-H+ OCH$_2$CONH$_2$), 8.01 (1H, d, J=8.66 Hz, 5-H), 11.92 (1H, bs, NH). m/z (CI$^+$), 329, (M+1).

EXAMPLE 35

7-Chloro-4-methoxyaminocarbonylmethoxy-3-phenyl-2(1H)-quinolone

To a solution of 4-carboxymethoxy-7-chloro-3-phenyl-2(1H)-quinolone (Example 15, 1.83 g) in tetrahydrofuran (150 ml) under nitrogen at room temperature, was added triethylamine (3.65 ml), O-methyl hydroxylamine hydrochloride (0.96 g), 1-hydroxybenzotriazole (1.15 g) and 1-(3 dimethylaminopropyl)-3-ethyl carbodiimide (1.73 g). The reaction mixture was stirred at room temperature for 16 h, then poured into water (150 ml) and extracted with ethyl acetate (3×100 ml). The combined organic layers were washed with water (1×100 ml), 1N citric acid (1×100 ml), brine (1×100 ml) and a saturated sodium hydrogen carbonate solution (1×50 ml), dried (MgSO$_4$), filtered and the solvent was removed in vacuo to leave a solid residue. Recrystallisation from ethyl acetate gave the title compound (0.12 g). Mp 205°–207° C. m/z (CI$^+$), 359, (m+1). $^1$H NMR (360 MHz, DMSO-$d_6$) δ 3.32 (3H, s, NHOCH$_3$), 3.93 (2H, s, OCH$_2$CONHOCH$_3$), 7.23 (1H, dd, J=8.63 Hz, J=1.83 Hz, 6-H), 7.36–7.45 (6H, m, Ph+8-H), 8.00 (1H, d, J=8.63 Hz, 5-H), 11.26 (1H, bs, OCH$_2$CONHOCH$_3$), 11.94 (1H, bs, NH). Found: C, 60.57; H, 4.26; N, 7.82; $C_{18}H_{15}N_2O_4Cl$ requires C, 60.26; H, 4.21; N, 7.81%.

EXAMPLE 36

7-Chloro-4-(2-carboxy)ethyl-3-phenyl-2(1H)-quinolone

A. 5-Chloro-2-hydroxymethyl aniline

To a solution of 4-chloro-2-nitro benzyl alcohol (25.00 g) in methanol (1 ltr) under nitrogen at room temperature, was added platinum on sulfided carbon (2.5 g, 10% by wt). The reaction mixture was shaken under 50 psi of hydrogen until the theoretical uptake of hydrogen had occurred. Filtration, then removal of the solvent in vacuo afforded the desired compound as a solid (21.00 g). δ (360 MHz, DMSO-$d_6$) 4.35 (2H, d, J=4.95 Hz, $CH_2OH$), 5.17 (1H, t, J=4.95 Hz, $CH_2OH$), 6.77 (1H, dd, J=7.98 Hz, J=2.18 Hz, 4-H), 7.06 (1H, d, J=2.18 Hz, 6-H), 7.18 (1H, d, J=7.98 Hz, 3-H), 8.08 (1H, bs, $NH_2$), 8.47 (1H, bs, NH).

B. N-(Benzylcarbonyl)-5-chloro-2-hydroxymethyla-niline

To a suspension of 5-chloro-2-hydroxymethyl aniline (8.00 g) in dichloromethane (400 ml) under nitrogen at room temperature, was added triethylamine (15.6 ml). The reaction mixture was cooled to 0° C. then phenyl acetyl chloride (14.80 ml) was added dropwise over 10 mins, and the reaction mixture was allowed to warm to room temperature and stir for 2 h. The mixture was washed with 1N HCl (2×250 ml) and brine (1×250 ml). The aqueous layers were re-extracted using $CH_2Cl_2$ (1×250 ml) and the combined organic layers were dried ($MgSO_4$), filtered and the solvent was removed under vacuum to leave an orange solid. The solid was suspended in MeOH (400 ml), sodium hydroxide (2.20 g) was added in water (100 ml) and the reaction mixture was allowed to stir under gentle heating (50° C.) for 45 mins. The methanol was removed in vacuo, then the aqueous residue was extracted with dichloromethane (1×200 ml) and the organic layer was washed with brine (1×150 ml) and saturated sodium hydrogen carbonate solution (1×150 ml). The organic layer was dried ($MgSO_4$), filtered and the solvent was removed under vacuum to leave a solid. Trituration with diethyl ether gave the required compound (10.00 g).

C. 2-(Benzylcarbonylamino)-4-chloro benzaldehyde

To a solution of N-(benzylcarbonyl)-5-chloro-2-hydroxymethyl aniline (15.50 g) in dichloromethane (400 ml) under nitrogen at room temperature, was added pyridinium chlorochromate (24.30 g) and crushed 4 Å molecular sieves (0.50 g). The reaction mixture was stirred at room temperature for 90 mins, then ethyl acetate added, and the solution was filtered through a 2 inch plug of silica gel. The solvent was removed in vacuo and the material was redissolved in ethyl acetate and filtered through silica gel. Removal of the solvent under vacuum and trituration of the solid residue with diethyl ether gave the desired compound (10.50 g). δ (360 MHz, DMSO-$d_6$) 3.82 (2H, s, $NHCOCH_2Ph$), 7.27–7.39 (6H, m, Ph+5-H), 7.87 (1H, d, J=8.30 Hz, 6-H), 8.36 (1H, d, J=1.87 Hz, 3-H), 9.89 (1H, s, CHO), 10.97 (1H, bs, $NHCOCH_2Ph$).

D. N-Benzylcarbonyl-5-chloro-2-(3-ethoxycarbonyl-1-hydroxy-propyl)-aniline

To a solution of 2-(benzylcarbonylamino)-4-chlorobenzaldehyde (10.50 g) in dichloromethane (100 ml) under nitrogen at 78° C. was added $TiCl_4$ (4.3 ml) then 1-1-[1-(Ethoxy cyclopropane)oxy]-trimethylsilane (8.80 ml) in dichloromethane (30 ml) was added dropwise, over 10 mins. The reaction mixture was stirred at −78° C. for 15 mins, then allowed to warm to 0° C. and stirred for 45 mins, then allowed to warm to room temperature and stirred for 3 h. A saturated solution of ammonium chloride was added (100 ml) then the aqueous and organic layers were partitioned and the aqueous layer was re-extracted with dichloromethane (2×75 ml). The combined organic layers were dried ($MgSO_4$), filtered and the solvent was removed in vacuo. Purification by silica gel flash chromatography (using 20–60% EtOAc in hexane as eluent) gave the desired compound as an oil (7.78 g). δ (360 MHz, DMSO-$d_6$) 1.16 (3H, t, J=7.10 Hz, $CH(OH)CH_2CH_2CO_2CH_2CH_3$), 1.60 (2H, m, $CH(OH)CH_2CH_2CO_2Et$), 2.15–2.33 (2H, m, $CH(OH)CH_2CH_2CO_2Et$), 3.70 (2H, s, $NHCOCH_2Ph$), 4.01 (2H, q, J=7.10 Hz, $CH(OH)CH_2CH_2CO_2CH_2CH_3$), 4.68 (1H, bs, $CH(OH)CH_2$), 5.73 (1H, bs, $CH(OH)CH_2$), 7.16–7.34 (7H, m, Ph+4-H+6-H), 7.79 (1H, d, 3-H), 9.68 (1H, bs, $NHCOCH_2Ph$).

E. N-(Benzylcarbonyl)-5-chloro-2-[(3-ethoxycarbonyl-1-carbonyl)propyl]aniline To a solution of N-benzylcarbonyl)-5-chloro-2-(3-ethoxycarbonyl-hydroxypropyl)-aniline (8.80 g) in dichloromethane (400 ml) under nitrogen at room temperature, was added pyridinium chlorochromate (10.10 g) and crushed 4 Å molecular sieves (0.50 g). The reaction mixture was stirred at room temperature for 3 h, then a further aliquot of pyridinium chlorochromate was added (2.53 g) and the reaction mixture was stirred at room temperature for a further 16 h. Ethyl acetate (100ml) was added, then the mixture was filtered through a 1 inch plug of silica gel and the solvent was removed in vacuo to give the desired compound as a solid (8.00 g). δ (360 MHz, DMSO-$d_6$) 1.19 (3H, t, J=7.1 Hz), 2.59 (2H, t, J=6.4 Hz), 3.26 (2H, t, J=6.4 Hz), 3.76 (2H, s), 4.06 (2H, q, J=7.1 Hz), 7.27–7.37 (6H, m), 8.06 (1H, d, J=8.6 Hz), 8.47 (1H, s), 11.30 (1H, s); m/z ($CI^+$) 374 (M+1).

F. 7-Chloro-4-[(2-ethoxycarbonyl)ethyl]-3-phenyl-2(1H)-quinolone

To a solution of N-(benzylcarbonyl)-5-chloro-3-[(3-ethoxycarbonyl-1-carbonyl)propyl]-aniline (8.00 g, 21.42 mmol) in EtOH (200 ml) at room temperature was added an 80% dispersion of NaH (1.42 g). The reaction mixture was stirred at room temperature for 1 h, then ethanolic hydrogen chloride was added (50 ml) and the solvent was removed in vacuo to leave a solid residue. The residue was partitioned between ethyl acetate (200 ml) and $H_2O$ (200 ml) and the aqueous was back extracted with ethyl acetate (1×200 ml). The combined organic layers were washed with water (1×150 ml) and brine (1×150 ml), dried ($MgSO_4$), filtered and the solvent was removed in vacuo to give the desired compound (7.6 g). δ (360 MHz, DMSO-$d_6$) 1.08 (3H, t, J=7.11 Hz, $CH_2CH_2CO_2CH_2CH_3$), 2.43 (2H, t, J=8.25 Hz, $CH_2CH_2CO_2Et$), 2.86 (2H, t, J=8.25 Hz, $CH_2CH_2CO_2Et$), 3.95 (2H, t, J=7.11 Hz, $CH_2CH_2CO_2CH_2CH_3$), 7.22–7.47 (7H, m, Ph+6-H+8-H), 7.81 (1H, d, J=9.76 Hz, 5-H), 11.98 (1H, bs, NH).

G. 7-Chloro-4-(2-carboxy)ethyl-3-phenyl-2(1H)-1-quinolone

To a solution of 7-chloro-4-[(2-ethoxycarbonyl)ethyl]-3-phenyl-2(1H)-quinolone (7.60 g) in ethanol (500 ml) at room temperature was added sodium hydroxide and water (100 ml). The reaction mixture was stirred at room temperature for 3 h, then a further aliquot of sodium hydroxide (3.50 g) was added and the reaction mixture was stirred at room temperature for a further 16 h. The ethanol was removed in vacuo and the aqueous residue was acidified to pH 1 using 5N HCl. Filtration of the emerging precipitate gave the desired compound (5.50 g); mp 316°–318° C. Found: C, 65.99; H, 4.36; N, 4.29. $C_{18}H_{14}ClNO_3$ requires C, 65.96; H, 4.31; N, 4.27%. δ (360 MHz, DMSO-d$_6$) 2.37 (2H, t, J=8.6 Hz), 2.83 (2H, t, J=8.6 Hz), 7.22–7.28 (3H, m), 7.36–7.46 (4H, m), 7.82 (1H, d, J=8.7 Hz), 11.95 (1H, br, s). m/z (CI$^+$) 328 (M+1).

EXAMPLE 37

7-Chloro-4-[(2-methoxycarbonyl)ethyl]-3-phenyl-2(1H)-quinolone

7-Chloro-4-[(2-ethoxycarbonyl)ethyl]-3-phenyl-2(1H)-quinolone (Example 36, part F, 1.17 g) was dissolved in a saturated solution of hydrogen chloride in dry methanol (100 ml) and stood at room temperature for 3 h. Evaporation of the solvents and recrystallisation of the residue from methanol gave the required product (0.42 g); mp 193°–194° C.; Found: C, 67.38; H, 4.75; N, 4.11. C$_{19}$H$_{16}$ClNO$_3$. 0.1H$_2$O requires C, 67.18; H, 5.01; N, 4.00%. δ (360 MHz, DMSO-d$_6$) 2.47 (2H, t, J=8.4 Hz), 2.88 (2H, t, J=8.4 Hz), 3.52 (3H, s), 7.21–7.27 (3H, m), 7.36–7.46 (4H, m), 7.82 (1H, d, J=8.8 Hz), 11.94 (1H, br, s); m/z (CI$^+$) 342 (M+1).

EXAMPLE 38

4-(2-Aminocarbonyl)ethyl-7-chloro-3-phenyl-2(1H)-quinolone

To a solution of 7-chloro-4-(2-carboxy)ethyl-3-phenyl-2(1H)-quinolinone (1.70 g) in tetrahydrofuran (100 ml) under nitrogen at room temperature, was added triethylamine (3.25 ml), ammonium acetate (0.80 g), 1-hydroxybenzotriazole (1.05 g) and 1-(3-N,N dimethylaminopropyl)-3-ethyl carbodiimide (1.49 g). The reaction mixture was stirred at room temperature for 24 h, the more ammonium acetate (0.20 g), 1-hydroxybenzotriazole (0.35 g) and 1-(3-N,N dimethylaminopropyl)-3-ethyl carbodiimide (0.49 g) was added. The reaction mixture was stirred at room temperature for a further 48 h, then poured into water (100 ml) and extracted with ethyl acetate (3×100 ml). The combined organic layers were washed with 1N citric acid (1×100 ml), water (1×100 ml), saturated sodium hydrogen carbonate solution (1×100 ml) and brine (1×100 ml) then dried (MgSO$_4$), filtered and the solvent was removed in vacuo. Recrystallisation from MeOH gave the title compound (0.05 g). Mp 297°–299° C. Found: C, 66.31; H, 5.95; N, 7.46; C$_{19}$H$_{19}$N$_2$O$_2$Cl 0.1C$_6$H$_{14}$ 0.6H$_2$O requires C, 65.97; H, 5.93; N, 7.85%. δ (360 MHz, DMSO-d$_6$) 2.21 (2H, t, J=8.30 Hz, CH$_2$CH$_2$CONH$_2$), 2.77 (2H, t, J=8.30 Hz, CH$_2$CH$_2$CONH$_2$), 6.78 (1H, bs, CH$_2$CH$_2$CONH$_2$), 7.21–7.46 (8H, m, Ph+6-H+8-H+CONH$_2$), 7.81 (1H, d, J=8.84 Hz, 5-H), 11.92 (1H, bs, NH). m/z (CI$^+$), 327, (M+1).

EXAMPLE 39

7-Chloro-4-(2-cyanoethyl)-3-phenyl-2(1H)-quinolone

To a solution of 4-(2-aminocarbonyl)ethyl-7-chloro-3-phenyl-2(1H)-quinolone (Example 38, 0.60 g) in tetrahydrofuran (80 ml) under nitrogen at 0° C., was added triethylamine (1.13 ml) followed by trifluoroacetic anhydride (0.70 ml). The reaction mixture was stirred at 0° C. for 45 mins, then poured into water (100 ml) and extracted with diethyl ether (2×100 ml). The combined organic layers were washed with water (1×100 ml) and brine (1×100 ml), dried (MgSO$_4$), filtered and the solvent was removed in vacuo. Recrystallisation from a water/methanol mixture gave the title compound (0.08 g). Mp 252°–254° C. Found: C, 70.26; H, 4.38; N, 9.04; C$_{18}$H$_{13}$N$_2$OCl requires C, 70.02; H, 4.24; N, 9.07%. δ (360 MHz, DMSO-d$_6$) 2.66 (2H, t, J=7.65 Hz, CH$_2$CH$_2$CN), 2.96 (2H, t, J=7.65 Hz, CH$_2$CH$_2$CN), 7.24–7.48 (7H, m, Ph+6-H+8-H), 7.91 (1H, d, J=8.79 Hz, 5-H), 12.03 (1H, bs, NH). m/z (CI$^+$), 327, (M+1).

EXAMPLE 40

7-Chloro-3-phenyl-4-(2-tetrazol-5-yl)ethyl-quinolin-2(1H)-one

To a solution of 7-chloro-4-(2-cyanoethyl)-3-phenyl-quinolin-2(1H)-one (Example 39, 0.45 g) in 1-methyl-2-pyrrolidinone (50 ml) under nitrogen at room temperature, was added sodium azide (0.28 g) followed by triethylamine hydrochloride (0.30 g). The reaction mixture was heated to 150° C. and stirred for 48 h. After allowing to cool, the mixture was poured into water (100 ml), acidified to pH 1 with concentrated HCl and extracted with ethyl acetate (3×75 ml). The combined organic layers were extracted with 1N sodium hydroxide (3×75 ml) and the combined aqueous phases were washed with diethyl ether (2×75 ml), then acidified to pH 1 using concentrated HCl. The aqueous layer was extracted with ethyl acetate (3×75 ml) and the combined organic layers were dried (MgSO$_4$), filtered and the solvent was removed in vacuo to leave a solid residue. Recrystallisation from a water/methanol mix then from ethyl acetate gave the title compound (0.05 g). Mp 231°–233° C. Found: C, 61.31; H, 4.20; N, 19.41; C$_{18}$H$_{14}$N$_5$OCl. 0.1 H$_2$O requires C, 61.14; H, 4.05; N, 19.81%. δ (360 MHz, DMSO-d$_6$) δ 3.05 (4H, bs, CH$_2$CH$_2$Tet)), 7.10–7.42 (7H, m, Ph+6-H+8-H), 7.86 (1H, d, J=8.73 Hz, 5-H), 12.00 (1H, bs, NH). m/z (CI$^+$), 352, (M+1).

EXAMPLE 41

7-Chloro-4-[2-(3-methyl-1,2,4-oxadiazol-5-yl)ethyl]-3-phenyl-2(1H)-quinolone To a solution of acetamide oxime (0.26 g) in tetrahydrofuran (50 ml) under nitrogen at room temperature was added an 80% dispersion of sodium hydride (0.14 g). The reaction mixture was heated to 60° C., stirred for 90 mins then 7-chloro-4-(2-methoxycarbonyl)ethyl)-3-phenyl-2(1H)-quinolone was added (Example 37, 0.50 g) and the reaction mixture was stirred at 60° C. for 3 h. After allowing to cool, the mixture was poured into water (100 ml) and extracted with ethyl acetate (3×75 ml). The combined organic layers were washed with 1N citric acid (1×75 ml), water (1×75 ml), saturated sodium hydrogen carbonate solution (1×75 ml) and brine (1×75 ml), then dried (MgSO$_4$), filtered and the solvent was removed in vacuo to leave a solid residue. Recrystallisation from an ethyl acetate/methanol mixture gave the title compound as a white solid (0.08 g). Mp 235°–238° C. Found: C, 65.38; H, 4.41; N, 11.35; C$_{20}$H$_{16}$N$_3$O$_2$Cl requires C, 65.67; H, 4.41; N, 11.49%. δ (360 MHz, DMSO-d$_6$) 2.25 (3H, s, CH$_3$), 3.04 (4H, m, CH$_2$, CH$_2$), 7.16 (1H, dd, J=8.77 Hz, J=1.33 Hz, 6-H), 7.18–7.44 (6H, m, Ph+8-H), 7.87 (1H, d, J=8.77 Hz, 5-H), 12.00 (1H, bs, NH). m/z (CI$^-$), 365 (m).

Tablet Preparation

Tablets containing 1.0, 2.0, 25.0, 26.0, 50.0 and 100.0 mg, respectively of the following compounds are prepared as illustrated below:

4-Amino-7-chloro-3-(3-phenoxyphenyl)-2(1H)-quinolone

7-Chloro-4-cyanomethoxy-3-(3-phenoxy)phenyl-2(1H)-quinolone

7-Chloro-4-[2-(3-methyl-1,2,4-oxadiazol-5-yl)ethyl]-3-phenyl-2(1H)-quinolone

TABLE FOR DOSES CONTAINING FROM 1–25 MG OF THE ACTIVE COMPOUND

|  | Amount-mg | | |
| --- | --- | --- | --- |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

TABLE FOR DOSES CONTAINING FROM 26–100 MG OF THE ACTIVE COMPOUND

|  | Amount-mg | | |
| --- | --- | --- | --- |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

We claim:

1. A method for the treatment and/or prevention of conditions which require the administration of a selective non-competitive antagonist of NMDA receptors, which comprises administering to a patient in need of such treatment an effective amount of a compound of formula I or a pharmaceutically acceptable salt thereof or a prodrug thereof:

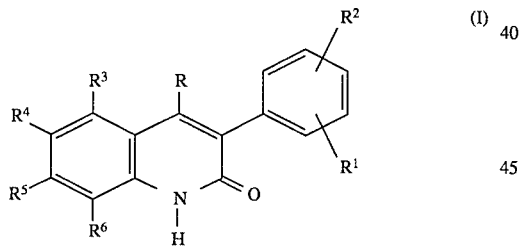

(I)

wherein

R represents a hydrogen atom, an amino group, a carboxy or $C_{2-6}$ alkoxycarbonyl group, or a group of formula -A-B-E, in which A represents a chemical bond, an oxygen or sulphur atom, or an —NH— group;

B represents a carbonyl (C=O) or sulphonyl ($SO_2$) group, or a straight or branched alkylene chain containing from 1 to 6 carbon atoms: and E represents $C_{1-6}$ alkyl, $C_{2-6}$ alkenyl, $C_{2-6}$ alkynyl, cyano, phenyl, tetrazolyl, methyloxadiazolyl, —$NR^aR^b$, —$COR^a$, —$C(=N.OR^a)R^b$, —$CO_2R^a$, —$CONR^aR^b$, —$CONR^a.OR^b$ or —$CH_2CO_2R^a$;

$R^1$ and $R^2$ independently represent hydrogen, hydrocarbon selected from the group consisting of: $C_{1-6}$alkyl, $C_{2-6}$alkenyl, $C_{2-6}$alkynyl, $C_{3-7}$cycloalkyl, $C_{3-7}$cycloalkyl($C_{1-6}$)alkyl, aryl being phenyl or naphthyl, aryl($C_{1-6}$)alkyl, aryl($C_{2-6}$)alkenyl and aryl($C_{2-6}$)alkynyl; halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$;

one of $R^3$, $R^4$, $R^5$ and $R^6$ represents hydrocarbon, as defined above, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$, and the other three of $R^3$, $R^4$, $R^5$ and $R^6$ independently represent hydrogen, hydrocarbon, as defined above, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon, as defined above.

2. A pharmaceutical composition comprising a compound of formula IA or a pharmaceutically acceptable salt thereof or a prodrug thereof:

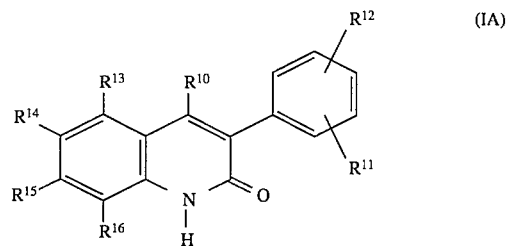

(IA)

wherein $R^{10}$ represents a hydrogen atom, an amino group, a carboxy or $C_{2-6}$ alkoxycarbonyl group, or a group of formula -A-B-E, in which A represents a chemical bond, an oxygen or sulphur atom, or an —NH— group;

B represents a carbonyl (C=O) or sulphonyl ($SO_2$) group, or a straight or branched alkylene chain containing from 1 to 6 carbon atoms; and E represents $C_{1-6}$ alkyl, $C_{2-6}$ alkenyl, $C_{2-6}$ alkynyl, cyano, phenyl, tetrazolyl, methyloxadiazolyl, —$NR^aR^b$, —$COR^a$, —$C(=N.OR^a)R^b$, —$CO_2R^a$, —$CONR^aR^b$, —$CONR^a.OR^b$ or —$CH_2CO_2R^a$;

$R^{11}$ and $R^{12}$ independently represent hydrogen, hydrocarbon selected from the group consisting of: $C_{1-6}$alkyl, $C_{2-6}$alkenyl, $C_{2-6}$alkynyl, $C_{3-7}$cycloalkyl, $C_{3-7}$cycloalkyl($C_{1-6}$)alkyl, aryl being phenyl or naphthyl, aryl($C_{1-6}$)alkyl, aryl($C_{2-6}$)alkenyl and aryl($C_{2-6}$)alkynyl; halogen, cyano, trifluoromethyl, nitro, —$OR^a$, —$SR^a$, —$SO_2NR^aR^b$, —$NR^aR^b$, —$NR^aCOR^b$, —$NR^aCO_2R^b$, —$COR^a$, —$CO_2R^a$ or —$CONR^aR^b$;

one of $R^{13}$, $R^{14}$, $R^{15}$ and $R^{16}$ represents hydrocarbon, as defined above, halogen, cyano, trifluoromethyl, nitro, —$OR^a$, —$SR^a$, —$SOR^a$, —$SO_2R^a$, —$SO_2 NR^aR^b$, —$NR^aR^b$, —$NR^aCOR^b$, —$NR^aCO_2 R^b$, —$COR^a$, —$CO_2R^a$ or —$CONR^aR^b$, and the other three of $R^{13}$, $R^{14}$, $R^{15}$ and $R^{16}$ independently represent hydrogen, hydrocarbon as defined above, halogen, cyano, trifluoromethyl, nitro, —$OR^a$, —$SR^a$, —$SOR^a$, —$SO_2R^a$, —$SO_2NR^aR^b$, —$R^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon as defined above;

provided that, when $R^{10}$ represents a straight or branched alkoxy group containing 2 to 4 carbon atoms and $R^{11}R^{12}$, $R^{13}$, $R^{14}$ and $R^{16}$ each represents hydrogen, then $R^{15}$ does not represent an unsubstituted straight or branched alkoxy group containing 2 to 10 carbon atoms or a straight or branched alkoxy group containing 1 to 6 carbon atoms having at least one substituent selected from hydroxy, carboxy and carbamoyl;

in association with one or more pharmaceutically acceptable carriers and/or excipients.

3. A composition as claimed in claim 2 wherein the active ingredient is selected from:

7-chloro-3-(2-methoxyphenyl)-2(1 H)-quinolone;

or a pharmaceutically acceptable salt or prodrug thereof.

4. A compound of formula IB or a salt or prodrug thereof:

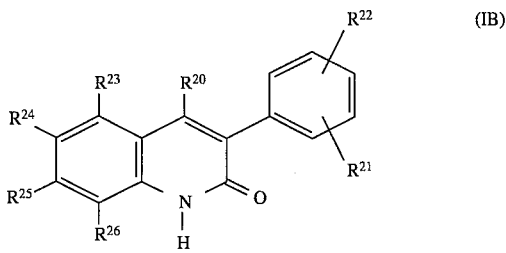

(IB)

wherein $R^{20}$ represents a hydrogen atom, an amino group, a carboxy or $C_{2-6}$ alkoxycarbonyl group, or a group of formula -A-B-E, in which A represents a chemical bond, an oxygen or sulphur atom, or an —NH— group;

B represents a carbonyl (C=O) or sulphonyl ($SO_2$) group, or a straight or branched alkylene chain containing from 1 to 6 carbon atoms; and E represents $C_{1-6}$ alkyl, $C_{2-6}$ alkenyl, $C_{2-6}$ alkynyl, cyano, phenyl, tetrazolyl, methyloxadiazolyl, —$NR^aR^b$, —$COR^a$, —C(=N.$OR^a$)$R^b$, —$CO_2R^a$, —$CONR^aR^b$, —$CONR^a.OR^b$ or —$CH_2CO_2R^a$;

$R^{21}$ and $R^{22}$ independently represent hydrogen, hydrocarbon selected from the group consisting of: $C_{1-6}$alkyl, $C_{2-6}$alkenyl, $C_{2-6}$alkynyl, $C_{3-7}$cycloalkyl, $C_{3-7}$cycloalkyl($C_{1-6}$)alkyl, aryl being phenyl or naphthyl, aryl ($C_{1-6}$)alkyl, aryl($C_{2-6}$)alkenyl and aryl($C_{2-6}$)alkynyl; halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$;

one of $R^{23}$, $R^{24}$, $R^{25}$ and $R^{26}$ represents halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl, and the other three of $R^{23}$, $R^{24}$, $R^{25}$ and $R^{26}$ independently represent hydrogen, halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl;

$R^a$ and $R^b$ independently represent hydrogen, or hydrocarbon as defined above;

provided that, when $R^{21}$ and $R^{22}$ each represents hydrogen, then:

(i) $R^{25}$ does not represent an unsubstituted straight or branched alkoxy group containing 2 to 10 carbon atoms or a straight or branched alkoxy group containing 1 to 6 carbon atoms having at least one substituent selected from hydroxy, carboxy and carbamoyl when $R^{20}$ represents a straight or branched alkoxy group containing 2 to 4 carbon atoms and $R^{23}$, $R^{24}$ and $R^{26}$ each represents hydrogen; and (ii) $R^{20}$ does not represent carboxy when $R^{24}$ is iodo and $R^{23}$, $R^{25}$ and $R^{26}$ each represents hydrogen; and (iii) $R^{20}$ does not represent amino or benzylamino when $R^{25}$ represents methyl or methoxy and $R^{23}$, $R^{24}$ and $R^{26}$ each represent hydrogen;

provided also that when $R^{21}$ is 2'-methoxy and $R^{22}$, $R^{23}$ and $R^{26}$ each represents hydrogen, then:

(i) $R^{20}$ does not represent hydrogen or carboxy when one of $R^{24}$ and $R^{25}$ represents fluoro or chloro and the other is hydrogen; and (ii) $R^{20}$ does not represent carboxy when one of $R^{24}$ and $R^{25}$ represents bromo or iodo and other is hydrogen.

5. A compound as claimed in claim 4 represented by formula IIA or salt and prodrug thereof:

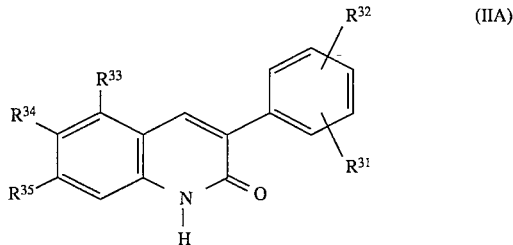

(IIA)

wherein $R^{31}$ represents $C_{1-6}$ alkyl, $C_{2-6}$ alkenyl, $C_{2-6}$ alkynyl, aryl, aryl($C_{2-6}$)alkyl, aryl($C_{2-6}$)alkenyl, aryl($C_{2-6}$)alkynyl, $C_{1-6}$ alkoxy, $C_{2-6}$ alkenyloxy, aryloxy, aryl($C_{1-6}$)alkoxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, or $C_{2-7}$ alkoxycarbonyl, any of which groups may be optionally substituted by $C_{1-6}$alkyl, morpholinyl($C_{1-6}$)alkyl, hydroxy, $C_{1-6}$alkoxy, $C_{1-6}$alkoxy($C_{1-6}$)alkyl, $C_{1-6}$alkoxy($C_{1-6}$)alkoxy, $C_{1-6}$alkylthio and di($C_{1-6}$)alkylamino; or hydrogen, halogen, cyano, trifluoromethyl, nitro, hydroxy, amino or carboxy; and $R^{32}$ represents $C_{1-6}$ alkyl, $C_{1-6}$ alkenyl, $C_{2-6}$ alkynyl, aryl, aryl($C_{1-6}$)alkyl, aryl($C_{2-6}$)alkenyl, aryl($C_{2-6}$)alkynyl, $C_{2-6}$ alkoxy, $C_{2-6}$ alkenyloxy, aryloxy, aryl($C_{1-6}$)alkoxy, $C_{2-6}$ alkylthio, arylthio, arylsulphonyl, arylamino, aryl($C_{2-6}$)alkylamino, di($C_{1-6}$)alkylamino, arylcarbonylamino, arylcarbonyl, or $C_{2-7}$ alkoxycarbonyl, any of which groups may be optionally substituted as defined above: or halogen, cyano, trifluoromethyl, nitro, hydroxy, amino or carboxy;

$R^{33}$ represents hydrogen, halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl;

$R^{34}$ represents hydrogen or halogen; and $R^{35}$ represents halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl.

6. A compound as claimed in claim 4 represented by formula IIB or salt and prodrug thereof:

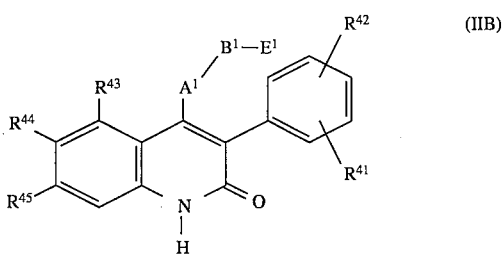

(IIB)

wherein $A^1$ represents a chemical bond, an oxygen atom or an —NH— group;

$B^1$ represents a carbonyl (C=O) or sulphonyl ($SO_2$) group, or a group of formula —$(CH_2)n$— in which n is 1, 2, 3 or 4; and $E^1$ represents $C_{1-6}$ alkyl, $C_{2-6}$ alkenyl, $C_{2-6}$ alkynyl, cyano, phenyl, tetrazolyl, methyloxadiazolyl, amino, $C_{1-6}$ alkylamino, di($C_{1-6}$)alkylamino, $C_{1-6}$ alkanoyl, oximino($C_{1-6}$)alkyl, $C_{1-6}$ alkyloximino($C_{1-6}$)alkyl, carboxy, $C_{2-6}$ alkoxycarbonyl, aminocarbonyl, di($C_{1-6}$)alkylaminocarbonyl, $C_{1-6}$ alkoxyaminocarbonyl, carboxymethyl or $C_{2-6}$ alkoxycarbonyl-methyl;

$R^{41}$ and $R^{42}$ independently represent $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, $C_{1-6}$ alkoxy, $C_{2-6}$ alkenyloxy, aryloxy, aryl($C_{1-6}$)alkoxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, or $C_{2-7}$ alkoxycarbonyl, any of which groups may be optionally substituted; or hydrogen, halogen, cyano, trifluoromethyl, nitro, hydroxy, amino or carboxy;

$R_{43}$ and $R_{44}$ independently represent hydrogen, halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl; and $R^{45}$ represents halogen, cyano, trifluoromethyl, nitro, hydroxy, amino, carboxy, $C_{2-6}$ alkenyl, $C_{1-6}$ alkylthio or $C_{2-7}$ alkoxycarbonyl.

7. A compound as claimed in claim 4 selected from:
7-chloro-3-(2-hydroxyphenyl)-2(1H)-quinolone;
7-chloro-3-(4-hydroxyphenyl)-2(1H)-quinolone;
3-(2-aminophenyl)-7-chloro-2(1H)-quinolone;
3-(3-carboxyphenyl)-7-chloro-2(1H)-quinolone;
4-carboxy-7-chloro-3-phenyl-2(1H)-quinolone;
4-carboxymethyl-7-chloro-3-phenyl-2(1H)-quinolone;
7-chloro-4-methoxycarbonylethyl-3-phenyl-2(1H)-quinolone;
4-carboxymethoxy-7-chloro-3-phenyl-2(1H)-quinolone;
7-chloro-4-methoxycarbonylmethoxy-3-phenyl-2(1H)-quinolone;
4-allyloxy-7-chloro-3-phenyl-2(1H)-quinolone;
4-amino-7-chloro-3-phenyl-2(1H)-quinolone;
4-amino-7-chloro-3-(2-methoxyphenyl)-2(1H)-quinolone;
4-amino-7-chloro-3-(3-phenoxyphenyl)-2(1H)-quinolone;
4-benzylamino-7-chloro-3-phenyl-2(1H)-quinolone;
7-chloro-4-(2-dimethylaminoethyl)amino-3-phenyl-2(1H)-quinolone;
7-chloro-4-(3-dimethylaminopropyl)amino-3-phenyl-2(1H)-quinolone;
4-acetylamino-7-chloro-3-phenyl-2(1H)-quinolone;
4-carboxymethylcarbonylamino-7-chloro-3-phenyl-2(1H)-quinolone;
4-carboxycarbonylamino-7-chloro-3-phenyl-2(1H)-quinolone;
7-chloro-4-methoxycarbonylcarbonylamino-3-phenyl-2(1H)-quinolone;
7-chloro-4-methylsulphonylamino-3-phenyl-2(1H)-quinolone;
7-chloro-3-phenyl-4-phenylsulphonylamino-2(1H)-quinolone;
7-chloro-4-methylcarbonylmethoxy-3-phenyl-2(1H)-quinolone;
7-chloro-4-(2-oximinopropyl)oxy-3-phenyl-2(1H)-quinolone;
7-chloro-3-phenyl-4-(2-propynyl)oxy-2(1H)-quinolone;
7-chloro-4-(2-methyloximinopropyl)oxy-3-phenyl-2(1H)-quinolone;
7-chloro-4-methoxycarbonylmethoxy-3-(3-phenoxyphenyl)-2(1H)-quinolone;
4-carboxymethoxy-7-chloro-3-(3-phenoxyphenyl)-2(1H)-quinolone;
7-chloro-4-cyanomethoxy-3-phenyl-2(1H)-quinolone;
7-chloro-4-cyanomethoxy-3-(3-phenoxyphenyl)-2(1H)-quinolone;
7-chloro-4-(N,N-dimethylaminocarbonyl)methoxy-3-phenyl-2(1H)-quinolone;
7-chloro-4-[2-(N,N-dimethylamino)ethoxy]-3-phenyl-2(1H)-quinolone;
4-aminocarbonylmethoxy-7-chloro-3-phenyl-2(1H)-quinolone;
7-chloro-4-methoxyaminocarbonylmethoxy-3-phenyl-2(1H)-quinolone;
7-chloro-4-(2-methoxycarbonylethyl)-3-phenyl-2(1H)-quinolone;
4-(2-carboxyethyl)-7-chloro-3-phenyl-2(1H)-quinolone;
4-(2-aminocarbonylethyl)-7-chloro-3-phenyl-2(1H)-quinolone;
7-chloro-4-(2-cyanoethyl)-3-phenyl-2(1H)-quinolone;
7-chloro-3-phenyl-4-[2-(1H-tetrazol-5-yl)ethyl]-2(1H)-quinolone;
7-chloro-4-[2-(3-methyl-1,2,4-oxadiazol-5-yl)ethyl]-3-phenyl-2(1H)-quinolone;
or a pharmaceutically acceptable salt or prodrug thereof.

* * * * *